(12) United States Patent
Tojo et al.

(10) Patent No.: US 9,125,811 B2
(45) Date of Patent: *Sep. 8, 2015

(54) NANOFIBER LAMINATE SHEET (75) Inventors: Takehiko Tojo, Tochigi (JP); Masataka Ishikawa, Tochigi (JP); Ritsuko Yamazaki, Tokyo (JP); Yuko Yago, Tokyo (JP); Motoaki Ito, Tokyo (JP); Yoshimi Yamashita, Tochigi (JP)

(73) Assignee: KAO CORPORATION, Tokyo (JP)

( * ) Notice: Subject to any disclaimer, the term of this patent is extended or adjusted under 35 U.S.C. 154(b) by 67 days.

This patent is subject to a terminal disclaimer.

(21) Appl. No.: 13/807,626

(22) PCT Filed: Jun. 28, 2011

(86) PCT No.: PCT/JP2011/064810
§ 371 (c)(1),
(2), (4) Date: Feb. 19, 2013

(87) PCT Pub. No.: WO2012/002390
PCT Pub. Date: Jan. 5, 2012

(65) Prior Publication Data
US 2013/0142852 A1    Jun. 6, 2013

(30) Foreign Application Priority Data

Jun. 29, 2010 (JP) ................. 2010-148377
Jun. 30, 2010 (JP) ................. 2010-150507
Jun. 30, 2010 (JP) ................. 2010-150545

(51) Int. Cl.
| | |
|---|---|
| *A61K 8/02* | (2006.01) |
| *A61K 9/70* | (2006.01) |
| *A61K 8/19* | (2006.01) |
| *B32B 5/26* | (2006.01) |
| *A61K 8/81* | (2006.01) |
| *A61Q 19/08* | (2006.01) |
| *A61Q 1/02* | (2006.01) |
| *A61K 8/73* | (2006.01) |
| *A61Q 1/00* | (2006.01) |
| *A61L 15/44* | (2006.01) |
| *A61K 8/67* | (2006.01) |

(52) U.S. Cl.
CPC ............ *A61K 8/0233* (2013.01); *A61K 8/027* (2013.01); *A61K 8/0208* (2013.01); *A61K 8/676* (2013.01); *A61K 8/73* (2013.01); *A61K 8/8129* (2013.01); *A61K 9/70* (2013.01); *A61K 9/7007* (2013.01); *A61L 15/44* (2013.01); *A61Q 1/00* (2013.01); *A61Q 1/02* (2013.01); *A61Q 19/08* (2013.01); *A61K 2800/412* (2013.01); *A61K 2800/413* (2013.01); *A61L 2400/12* (2013.01)

(58) Field of Classification Search
CPC ... A61K 8/0208; A61K 8/0233; A61K 8/027; A61K 8/8129; A61K 9/70; A61K 9/7007; B32B 5/26
See application file for complete search history.

(56) References Cited

U.S. PATENT DOCUMENTS

| | | | |
|---|---|---|---|
| 6,398,830 B1* | 6/2002 | Rhodes et al. ............... 55/385.1 |
| 8,642,172 B2* | 2/2014 | Tojo et al. ..................... 428/343 |
| 2004/0089602 A1* | 5/2004 | Heinrich et al. ............... 210/505 |
| 2005/0266760 A1 | 12/2005 | Chhabra et al. |
| 2007/0072959 A1* | 3/2007 | Nip ............................... 523/200 |
| 2008/0092457 A1* | 4/2008 | Malone et al. ................... 52/105 |
| 2008/0095748 A1* | 4/2008 | Kharazi et al. ............... 424/93.7 |
| 2008/0261043 A1 | 10/2008 | Greiner et al. |
| 2009/0202616 A1 | 8/2009 | Chong et al. |
| 2009/0221047 A1* | 9/2009 | Schindler et al. ............. 435/160 |
| 2010/0254961 A1 | 10/2010 | Nishio et al. |

FOREIGN PATENT DOCUMENTS

| | | |
|---|---|---|
| JP | 2003-341 A | 1/2003 |
| JP | 2003-228852 A | 8/2003 |
| JP | 2004-209580 A | 7/2004 |
| JP | 2005/290610 A | 10/2005 |
| JP | 2006-123360 A | 5/2006 |
| JP | 2007-30153 A | 2/2007 |
| JP | 2007-236551 A | 9/2007 |
| JP | 2007-528944 A | 10/2007 |
| JP | 2007-303020 A | 11/2007 |
| JP | 2008-514341 A | 5/2008 |
| JP | 2008-162098 A | 7/2008 |
| JP | 2008-163520 A | 7/2008 |
| JP | 2008/179629 A | 8/2008 |
| JP | 2008-190093 A | 8/2008 |
| JP | 2008-531860 A | 8/2008 |
| JP | 2008-213095 A | 9/2008 |
| JP | 2008-285793 A | 11/2008 |
| JP | 2009-263818 A | 11/2009 |
| JP | 2010-248665 A | 11/2010 |
| JP | 2011-132634 A | 7/2011 |
| KR | 10-2007-0099926 A | 10/2007 |
| WO | WO 02/32397 A2 | 4/2002 |
| WO | WO 2006/036130 A1 | 4/2006 |
| WO | WO 2007/142757 A2 | 12/2007 |
| WO | WO 2009/31620 A1 | 3/2009 |
| WO | WO 2009/120365 A2 | 10/2009 |

OTHER PUBLICATIONS

International Preliminary Report on Patentability for International Application No. PCT/JP2011/064810 (Form PCT/IB/373) dated Feb. 12, 2013.

(Continued)

*Primary Examiner* — Abigail Fisher
(74) *Attorney, Agent, or Firm* — Birch, Stewart, Kolasch & Birch, LLP (57) ABSTRACT

A nanofiber laminate sheet including a layer of a nanofiber of a water insoluble polymer and a layer of a water soluble polymer containing a cosmetic component or a medicinal component. The nanofiber is preferably colored. The layer of a water soluble polymer is preferably a layer of a nanofiber of the water soluble polymer containing the cosmetic component or the medicinal component. The nanofiber laminate sheet is suited for use as a cosmetic sheet for makeup.

9 Claims, 3 Drawing Sheets

(56) References Cited

OTHER PUBLICATIONS

Notification of Transmittal of Copies of Translation of the International Preliminary Report on Patentability for International Application No. PCT/JP2011/064810 (Form PCT/IB/338) dated Feb. 21, 2013.

Written Opinion of the International Searching Authority for International Application No. PCT/JP2011/064810 (Form PCT/ISA/237) dated Oct. 4, 2011.

International Search Report issued in PCT/JP2011/064810, mailed on Oct. 4, 2011.

Written Opinion of the International Searching Authority issued in PCT/JP2011/064810, mailed on Oct. 4, 2011.

International Preliminary Report on Patentability for International Patent Application No. PCT/JP2009/071559, dated Aug. 25, 2011.

International Search Report for International Patent Application No. PCT/JP2009/071559, dated Feb. 2, 2010.

Notice of Rejection for Japanese Patent Application No. 2009-293480, dated Jan. 8, 2013.

Supplementary European Search Report for European Patent Application No. 09835008.5, dated Jun. 29, 2012.

* cited by examiner

NANOFIBER LAMINATE SHEET

TECHNICAL FIELD

The present invention relates to a sheet having a nanofiber layer that is particularly suited to cosmetic or medical care.

BACKGROUND ART

Nanofibers are applied to the fields demanding optical characteristics such as high transparency, where the nano-size effect of nanofibers are taken advantage of. For example, nanofibers with a diameter equal to or below the wavelength of visible light provide transparent fabric. By the use of nanofibers the diameter of which is equal to the wavelength of visible light, structural color may be exhibited. Nanofibers have also been studied for their applicability to the fields demanding superabsorbent characteristics or high surface activity, where the high specific surface area effect of nanofibers is taken advantage of, and to the fields demanding mechanical characteristics such as tensile strength and electrical characteristics such as high conductivity, where the supramolecular arrangement effect of nanofibers is made use of Nanofibers having such characteristics have been used in the form of, for example, not only single fibers but aggregates (i.e., fabrics) or composites.

Applications of nanofibers that have been proposed include a cosmetic sheet comprising a network structure made of a water soluble polymer nanofiber and a cosmetic or a cosmetic component, such as ascorbic acid, held in the network structure as disclosed in patent literature 1 below. According to the disclosure, the cosmetic sheet is obtained by electrospinning a liquid prepared by mixing a cosmetic or a cosmetic component into a solution of a polymer dissolved in water or a solvent. The cosmetic sheet obtained by this method contains the cosmetic or cosmetic component inside the nanofiber. The literature alleges that the cosmetic sheet has not only improved adhesion or comfort to the user's face, hand, or leg but also storage stability.

Patent literature 1 also teaches incorporating particles into a nanofiber sheet. Incorporating particles in a nanofiber sheet is also described in Patent literatures 2 to 4 below. In this regard, patent literature 1 proposes a cosmetic sheet comprising a network structure formed of polymer-based nanofibers and metal particles as a cosmetic component supported by the network structure. Patent literature 2 describes incorporating particles of, e.g., kaolin, carbon black, titanium oxide, or talc into a nanofiber sheet. Patent literature 3 also describes a nanofiber sheet containing a pigment.

CITATION LIST

Patent Literature

Patent literature 1: JP 2008-179629A
Patent literature 2: WO 2009/031620A1
Patent literature 3: JP 2007-303020A
Patent literature 4: US 2005/266760A1

SUMMARY OF INVENTION

Technical Problem

A nanofiber prepared from a water soluble polymer exhibits higher water solubility than in its bulk form because of the larger specific surface area and dissolves with water, e.g., of perspiration when attached to skin. Such a nanofiber is unable to maintain its fibrous form while being attached to the skin so that the advantage of attaching the nanofiber to the skin is not sufficiently brought out. It is difficult to attach a nanofiber sheet to the skin with fingers because its surface dissolves.

Moreover, when the cosmetic sheet of patent literature 1 is attached to the skin of a user, it provides a less than sufficient sense of unity with the skin and produces a less than sufficient effect in concealing skin color unevenness, such as redness and freckles, or diminishing the appearance of fine skin unevenness, such as pores and fine lines. Patent literature 1 is silent on using the cosmetic sheet as a makeup article to be put on a face to improve the facial appearance.

With reference to incorporating particles into a nanofiber sheet, patent literature 1 makes no mention of the size of the particles to be incorporated. Patent literatures 2 and 3 do not refer to the size of the particles to be used, either. Considering that the particles are used as a pigment for nanofibers in patent literatures 2 and 3, the particle size appears to be smaller than the nanofiber thickness. The particles held by the nanofiber sheet disclosed in patent literature 4 are not fixed to the nanofibers per se, they are liable to come off.

The invention provides a nanofiber sheet that eliminates the above discussed disadvantages of conventional techniques.

Solution to Problem

The invention settles the above described problems by the provision of a nanofiber laminate sheet composed of a layer of a nanofiber of a water-insoluble polymer and a layer of a water-soluble polymer containing a cosmetic component or a medicinal component.

The invention settles the above problems by the provision of a nanofiber sheet having a nanofiber of a water insoluble polymer and a nanofiber of a water soluble polymer containing a cosmetic component or a medicinal component.

The invention also provides a method for applying makeup using a nanofiber laminate sheet provided with a base sheet. The method includes the steps of attaching the nanofiber laminate sheet provided with a base sheet to skin with the nanofiber laminate sheet side inside under a state that the surface of the nanofiber laminate sheet or the skin is wet, stripping the base sheet from the nanofiber laminate sheet to transfer the nanofiber laminate sheet to the skin, and shearing the fiber bonds at the periphery of the nanofiber laminate sheet transferred to the skin to smoothen the level difference between the nanofiber laminate sheet and the skin.

The invention also provides a method for applying makeup using a nanofiber sheet provided with a base sheet. The method includes the steps of attaching the nanofiber sheet lined with a base sheet to skin with the nanofiber sheet side inside under a state that the surface of the nanofiber sheet or the skin is wet, stripping the base sheet from the nanofiber sheet to transfer the nanofiber sheet to the skin, and shearing the fiber bonds at the periphery of the nanofiber sheet transferred to the skin to smoothen the level difference between the nanofiber sheet and the skin.

The invention includes the following subject matter.

[1] A nanofiber laminate sheet comprising a layer of a nanofiber of a water insoluble polymer and a layer of a water soluble polymer containing a cosmetic component or a medicinal component.

[2] The nanofiber laminate sheet set forth in [1], wherein the layer of a nanofiber is made of a nanofiber of a water insoluble polymer containing a coloring pigment, and the nanofiber laminate sheet is for use as a cosmetic sheet for makeup.

[3] The nanofiber laminate sheet set forth in [2], having an outer color with a hue of 5.0 R to 9.8 YR, a value of 5.0 to 8.0, and a chroma of 2.5 to 6.0 in the Munsell color system.
[4] The nanofiber laminate sheet set forth in [1], wherein the layer of a nanofiber contains a composite nanofiber comprising a nanofiber and a particle fixed to the nanofiber, and the particle has a particle size greater than the thickness of the nanofiber and is covered with a material constituting the nanofiber.
[5] The nanofiber laminate sheet set forth in [4], wherein the nanofiber of the composite nanofiber has a thickness of 10 to 3000 nm, and the particle has a particle size of 1 to 100 μm.
[6] The nanofiber laminate sheet set forth in [4] or [5], wherein the particle is a platy particle.
[7] The nanofiber laminate sheet set forth in [6], wherein the particle is talc, mica, or a clay mineral.
[8] The nanofiber laminate sheet set forth in [4] or [5], wherein the particle is a light scattering particle.
[9] The nanofiber laminate sheet set forth in any one of [1] to [8], wherein the layer of a water soluble polymer is a layer of a nanofiber.
[10] The nanofiber laminate sheet set forth in any one of [1] to [8], wherein the layer of a water soluble polymer is film or gel.
[11] The nanofiber laminate sheet set forth in any one of [1] to [10], wherein a base sheet is provided on one side of the nanofiber laminate sheet, and the base sheet is releasable from the nanofiber laminate sheet.
[12] The nanofiber laminate sheet set forth in any one of [1] to [11], wherein the water insoluble polymer is a polyvinyl butyral resin, completely saponified polyvinyl alcohol insolubilizable after conversion to a nanofiber, partially saponified polyvinyl alcohol crosslinkable when combined with a crosslinking agent after conversion to a nanofiber, an oxazoline-modified silicone such as a poly (N-propanoylethyleneimine)-grafted dimethylsiloxane/γ-aminopropylmethylsiloxane copolymer, zein (main protein of corn), polyester, polylactic acid (PLA), an acrylic resin such as a polyacrylonitrile resin or a polymethacrylic acid resin, a polystyrene resin, a polyethylene terephthalate resin, a polybutylene terephthalate resin, a polyurethane resin, a polyamide resin, a polyimide resin, or a polyamideimide resin.
[13] The nanofiber laminate sheet set forth in [12], wherein the water insoluble polymer is a polyvinyl butyral resin.
[14] The nanofiber laminate sheet set forth in [12], wherein the water insoluble polymer is completely saponified polyvinyl alcohol insolubilizable after conversion to a nanofiber.
[15] The nanofiber laminate sheet set forth in [12], wherein the water insoluble polymer is partially saponified polyvinyl alcohol crosslinkable when combined with a crosslinking agent after conversion to a nanofiber.
[16] The nanofiber laminate sheet set forth in any one of [1] to [15], wherein the water soluble polymer is a mucopolysaccharides, e.g., pullulan, hyaluronic acid, chondroitin sulfate, poly-γ-glutamic acid, modified corn starch, β-glucan, gluco-oligosaccharides, heparin, and keratosulfate, cellulose, pectin, xylan, lignin, glucomannan, galacturonic acid, psyllium seed gum, tamarind seed gum, gum arabic, tragacanth gum, soybean water-soluble polysaccharides, alginic acid, carrageenan, laminaran, agar (agarose), fucoidan, methyl cellulose, hydroxypropyl cellulose, and hydroxypropylmethyl cellulose, partially saponified polyvinyl alcohol (usable in the absence of a crosslinking agent), low-saponified polyvinyl alcohol, polyvinylpyrrolidone (PVP), polyethylene oxide, or sodium polyacrylate.
[17] The nanofiber laminate sheet set forth in [16], wherein the water soluble polymer is pullulan, partially saponified polyvinyl alcohol, low-saponified polyvinyl alcohol, polyvinylpyrrolidone, or polyethylene oxide.
[18] The nanofiber laminate sheet set forth in [17], wherein the water soluble polymer is pullulan.
[19] The nanofiber laminate sheet set forth in any one of [1] to [18], wherein the cosmetic component is ascorbic acid.
[20] The nanofiber laminate sheet set forth in any one of [1] to [19], wherein the nanofiber layer is formed solely of a water insoluble nanofiber containing the water insoluble polymer.
[21] The nanofiber laminate sheet set forth in any one of [1] to [20], containing a volatile functional agent having a vapor pressure of 13.3 Pa or less at 20° C.
[22] A method for applying makeup using the nanofiber laminate sheet set forth in [11] provided with a base sheet, comprising the steps of:
attaching the nanofiber laminate sheet provided with a base sheet to skin with the nanofiber laminate sheet side inside under a state that the surface of the nanofiber laminate sheet or the skin is wet,
stripping the base sheet from the nanofiber laminate sheet to transfer the nanofiber laminate sheet to the skin, and
shearing the fiber bonds at the periphery of the nanofiber laminate sheet transferred to the skin to smoothen the level difference between the nanofiber laminate sheet and the skin.
[23] A method for producing the nanofiber laminate sheet set forth in [2] comprising the steps of
preparing a stock solution for spraying by mixing a slurry of the coloring pigment dispersed in a liquid medium with a solution of the polymer, and
electrospinning the stock solution for spraying to deposit a nanofiber to form the layer of a nanofiber.
[24] The method set forth in [23], wherein the slurry contains at least one of a dispersant for the coloring pigment or a defoaming agent.
[25] A nanofiber sheet comprising a nanofiber of a water insoluble polymer and a nanofiber of a water soluble polymer containing a cosmetic component or a medicinal component.
[26] The nanofiber sheet set forth in [25], wherein the nanofiber of a water insoluble polymer contains a coloring pigment, and the nanofiber sheet is for use as a cosmetic sheet for makeup.
[27] The nanofiber sheet set forth in [26], having an outer color with a hue of 5.0 R to 9.8 YR, a value of 5.0 to 8.0, and a chroma of 2.5 to 6.0 in the Munsell color system.
[28] The nanofiber sheet set forth in [25], wherein the nanofiber of a water insoluble polymer contains a composite nanofiber composed of a nanofiber and a particle fixed to the nanofiber, and
the particle has a particle size greater than the thickness of the nanofiber and is covered with a material constituting the nanofiber.
[29] The nanofiber sheet set forth in [28], wherein the nanofiber of the composite nanofiber has a thickness of 10 to 3000 nm, and the particle has a particle size of 1 to 100 μm.
[30] The nanofiber sheet set forth in [28] or [29], wherein the particle is a platy particle.
[31] The nanofiber sheet set forth in [30], wherein the particle is talc, mica, or a clay mineral.
[32] The nanofiber sheet set forth in [28] or [29], wherein the particle is a light scattering particle.

[33] The nanofiber sheet set forth in any one of [25] to [32], wherein a base sheet is provided on one side of the nanofiber sheet, and the base sheet is releasable from the nanofiber sheet.

[34] The nanofiber sheet set forth in any one of [25] to [33], containing a volatile functional agent having a vapor pressure of 13.3 Pa or less at 20° C.

[35] A method for applying makeup using the nanofiber sheet set forth in [33] provided with a base sheet, comprising the steps of:

attaching the nanofiber sheet provided with a base sheet to skin with the nanofiber sheet side inside under a state that the surface of the nanofiber sheet or the skin wetted, stripping the base sheet from the nanofiber sheet to transfer the nanofiber sheet to the skin, and shearing the fiber bonds at the periphery of the nanofiber sheet transferred to the skin to smoothen the level difference between the nanofiber sheet and the skin.

[36] A method for producing the nanofiber sheet set forth in [26], comprising the steps of:

preparing a stock solution for spraying by mixing a slurry of the coloring pigment dispersed in a liquid medium with a solution of the polymer, and electrospinning the stock solution for spraying to deposit a nanofiber to form the layer of a nanofiber.

[37] The method set forth in [36], wherein the slurry contains at least one of a dispersant for the coloring pigment or a defoaming agent.

[38] A method for producing a nanofiber laminate sheet comprising a layer of a nanofiber of a water insoluble polymer and a layer of a water soluble polymer containing a cosmetic component or a medicinal component, and containing an easily volatile functional agent having a vapor pressure higher than 13.3 Pa at 20° C., the method comprising the step of applying the easily volatile functional agent to the layer of a nanofiber.

[39] A method for producing a nanofiber sheet comprising a nanofiber of a water insoluble polymer and a nanofiber of a water soluble polymer containing a cosmetic component or a medicinal component, and containing an easily volatile functional agent having a vapor pressure higher than 13.3 Pa at 20° C.

the method comprising the step of applying the easily volatile functional agent to the nanofiber.

[40] A method for producing a nanofiber laminate sheet comprising a layer of a nanofiber of a water insoluble polymer and a layer of a water soluble polymer containing a cosmetic component or a medicinal component, and containing an easily volatile functional agent having a vapor pressure higher than 13.3 Pa at 20° C., the method comprising the step of leaving the easily volatile functional agent to stand close to the layer of a nanofiber to cause the easily volatile functional agent to transfer to the layer of a nanofiber.

[41] A method for producing a nanofiber sheet comprising a nanofiber of a water insoluble polymer and a nanofiber of a water soluble polymer containing a cosmetic component or a medicinal component, and containing an easily volatile functional agent having a vapor pressure higher than 13.3 Pa at 20° C., the method comprising the step of leaving the easily volatile functional agent to stand close to the nanofibers to cause the easily volatile functional agent to transfer to the nanofibers.

[42] A method for producing the nanofiber sheet set forth in [25] comprising providing a first solution for forming the nanofiber of a water insoluble polymer and a second solution for forming the nanofiber of a water soluble polymer containing a cosmetic component or a medicinal component, simultaneously operating a first syringe and a second syringe in such a manner that the first solution is electrospun from the first syringe at a gradually increasing rate of ejection starting from 0 up to a predetermined rate, and the second solution is electrospun from the second syringe at a gradually decreasing rate of ejection starting from a predetermined rate to zero, so that the resulting nanofiber sheet has a composition continuously varying from the composition of the nanofiber of a water insoluble polymer to that of the nanofiber of a water soluble polymer in its thickness direction.

[43] The method set forth in [42], wherein the rate of ejection from the first syringe and that from the second syringe are each maintained constant.

Advantageous Effects of Invention

The nanofiber laminate sheet of the invention exhibits high adhesion to skin. Therefore, when used as, for example, a cosmetic sheet, the nanofiber laminate sheet of the invention is capable of doing a skin care and a makeup simultaneously. When used as, for example, a medical sheet, it is capable of simultaneously healing and protecting a wound.

It is particularly advantageous to use the nanofiber laminate sheet as a cosmetic sheet for makeup in that the sheet forms a good apparent sense of unity with the skin to which it is attached, and exerts an enhanced effect in diminishing skin tone unevenness due to redness, freckles, etc. or making fine unevenness of skin surface, such as fine lines and pores, less discernible.

DESCRIPTION OF EMBODIMENTS

[First Embodiment]

The invention will be described based on its preferred embodiments. A first embodiment of a nanofiber laminate sheet of the invention (hereinafter also simply referred to as a laminate sheet) is basically composed of a layer of a nanofiber of a water insoluble polymer (hereinafter also referred to as a water insoluble nanofiber layer) and a layer of a water soluble polymer (hereinafter also referred to as a water soluble layer). The water soluble layer is disposed on one side of the water insoluble nanofiber. The water soluble layer preferably adjoins the water insoluble nanofiber layer. For some uses, between the water insoluble nanofiber layer and the water soluble layer there may be a layer different from either.

The water insoluble nanofiber layer is preferably made solely of a nanofiber containing a water insoluble polymer. The nanofiber containing a water insoluble polymer will hereinafter referred to as a water insoluble nanofiber. The water insoluble nanofiber layer may contain other components in addition to the water insoluble nanofiber. The water insoluble nanofiber has a thickness usually of 10 to 3000 nm, preferably 10 to 1000 nm, in terms of circle equivalent diameter. The thickness of nanofibers is measured by, for example, observation using a scanning electron microscope (SEM). Specifically, a two-dimensional micrograph at a magnification of 10000 is processed by deleting defects (lumps of nanofibers, intersections of nanofibers, and polymer droplets), randomly choosing ten fibers, drawing a line perpendicular to the longitudinal direction of each fiber chosen, and directly reading the fiber diameter.

The length of the water insoluble nanofiber is not critical in the invention and may have any appropriate length depending on the method of manufacturing the water insoluble nanofiber. A water insoluble nanofiber is called "fiber" when it is 100 or more times as long as it is thick. The nanofibers may be unidirectionally or randomly aligned in the water insoluble nanofiber layer. While the water insoluble nanofiber is generally a solid fiber, a hollow water-insoluble nanofiber or a flattened or ribbon-like hollow water-insoluble nanofiber having a collapsed cross-section is useful as well. The water insoluble nanofiber may have its thickness varied along its longitudinal direction.

The water insoluble nanofiber layer may have a thickness decided as appropriate to the intended use of the laminate sheet of the first embodiment. For example, for use as attached to human skin, tooth, or gum, the thickness of the water insoluble nanofiber layer is preferably 50 nm to 1 mm, more preferably 500 nm to 500 μm. When the laminate sheet of the first embodiment of which the water insoluble nanofiber layer has a thickness in that range is used as a cosmetic sheet as described later, there will be little level difference between the edge of the laminate sheet and the user's skin, providing an improved appearance of unity of the laminate sheet with the skin. When the laminate sheet of the first embodiment is applied to an area of skin having fine unevenness, such as a wrinkled or porous part of skin, the area will look like fine-textured skin. The thickness of the water insoluble nanofiber layer may be measured using a contact thickness gauge Litematic VL-50A from Mitutoyo Corp. with a spherical carbide contact point of 5 mm in radius at a measuring force of 0.01 N. A load of 0.01 N is applied to the sheet in the thickness measurement.

The water insoluble nanofiber layer may have a basis weight decided as appropriate to the intended use of the laminate sheet of the first embodiment. For example, for use as attached to human skin, tooth, or gum or for use as a cosmetic sheet, the basis weight of the water insoluble nanofiber layer is preferably 0.01 to 100 g/m$^2$, more preferably 0.1 to 50 g/m$^2$.

The water insoluble nanofibers in the water insoluble nanofiber layer are bonded to one another at the intersections thereof or intertwined with one another, whereby the water insoluble nanofiber layer is self-supporting to maintain the sheet form by itself. Whether the nanofiber(s) is/are bonded to or intertwined with itself or one another depends on the method of manufacture.

The water insoluble nanofiber is prepared from a water insoluble polymer. For some applications of the laminate sheet, the water insoluble nanofiber may contain a small amount of a water soluble component. The water insoluble polymer may be a naturally occurring polymer or a synthetic polymer.

In the case where, as will be described hereinafter, the water insoluble nanofiber contains a coloring pigment, and the laminate sheet of the first embodiment is used as a cosmetic sheet that is to be attached to the skin of a user, it is desirable that the water insoluble nanofiber layer remain on the skin without dissolving even after the sheet is attached to the skin, considering that the sheet brings out its cosmetic effect as attached to the skin. From this viewpoint, the water insoluble nanofiber contains a water insoluble polymer to advantage.

When a nanofiber contains a water insoluble polymer, the water insoluble polymer functions as a material forming the skeleton of the nanofiber. Therefore, even after the laminate sheet of the first embodiment is attached to the user's skin, the nanofiber does not dissolve with the water, e.g., of perspiration and retains its fibrous shape.

As used herein, the term "water insoluble polymer" refers to a polymer having solubility such that, when a sample polymer weighing 1 g is immersed in 10 g of ion-exchanged water for 24 hours at 23° C. and atmospheric pressure, up to only less than 0.8 g of the immersed polymer can dissolve in the ion-exchanged water.

Examples of the water insoluble polymer constructing the water insoluble nanofiber include a polyvinyl butyral resin, polyvinyl alcohol (including completely saponified polyvinyl alcohol insolubilizable after conversion to a nanofiber and partially saponified polyvinyl alcohol crosslinkable when combined with a crosslinking agent (hereinafter described) after conversion to a nanofiber), an oxazoline-modified silicone such as a poly(N-propanoylethyleneimine)-grafted dimethylsiloxane/γ-aminopropylmethylsiloxane copolymer, zein (main protein of corn), polyester, polylactic acid (PLA), an acrylic resin such as a polyacrylonitrile resin or a polymethacrylic acid resin, a polystyrene resin, a polyethylene terephthalate resin, a polybutylene terephthalate resin, a polyurethane resin, a polyamide resin, a polyimide resin, and a polyamideimide resin. These water insoluble resins may be used either individually or in combination of two or more thereof. Preferred of them is a polyvinyl butyral resin for its solubility in relatively safe organic solvents and good electrospinnability into nanofibers. It is also preferred to use, in place of a polyvinyl butyral resin, completely saponified polyvinyl alcohol insolubilizable after conversion to a nanofiber, partially saponified polyvinyl alcohol crosslinkable when combined with a hereinafter described crosslinking agent after conversion to a nanofiber, an oxazoline-modified silicone such as a poly(N-propanoylethyleneimine)-grafted dimethylsiloxane/γ-aminopropylmethylsiloxane copolymer, water soluble polyester, or zein.

When the water insoluble nanofiber contains a water soluble polymer in addition to the water insoluble polymer, the ratio of the water soluble polymer to the sum of the water insoluble polymer and the water soluble polymer is preferably 30% or less, more preferably 1% to 30%, even more preferably 10% to 25%, by mass. The ratio of the water insoluble polymer used in combination is preferably more than 70%, more preferably up to 99%, even more preferably 80% to 90%, by mass.

The water insoluble nanofiber may further contain other components in addition to the water insoluble polymer. Such components include a crosslinking agent, a pigment, a filler, a fragrance, a surfactant, an antistatic agent, and a foaming agent. A pigment is used to color the water insoluble nanofiber as described later. When, in particular, the laminate sheet of the first embodiment is designed to be attached to human skin, it is preferred for the water insoluble nanofiber to have a coloration that matches the skin tone to cause the laminate sheet to blend with the user's skin more effectively. A crosslinking agent is used to crosslink and insolubilize, for example, the above referred to partially saponified polyvinyl alcohol.

The water soluble layer provided on one side of the water insoluble nanofiber layer is formed of a layer containing a water soluble polymer. As used herein, the term "water soluble polymer" denotes a polymer having solubility such that, when a sample polymer weighing 1 g is immersed in 10 g of ion-exchanged water for 24 hours at 23° C. and atmospheric pressure, at least 0.5 g of the immersed polymer dissolves in the ion-exchanged water. For some applications of the laminate sheet of the first embodiment, the water soluble layer may contain a small amount of a water insoluble component.

Examples of the water soluble polymer that can be used in the water soluble layer include naturally occurring polymers, such as mucopolysaccharides, e.g., pullulan, hyaluronic acid, chondroitin sulfate, poly-γ-glutamic acid, modified corn starch, β-glucan, gluco-oligosaccharides, heparin, and keratosulfate, cellulose, pectin, xylan, lignin, glucomannan, galacturonic acid, psyllium seed gum, tamarind seed gum, gum arabic, tragacanth gum, soybean water-soluble polysaccharides, alginic acid, carrageenan, laminaran, agar (agarose), fucoidan, methyl cellulose, hydroxypropyl cellulose, and hydroxypropylmethyl cellulose; and synthetic polymers, such as partially saponified polyvinyl alcohol (when used in the absence of a crosslinking agent hereinafter described), low-saponified polyvinyl alcohol, polyvinylpyrrolidone (PVP), polyethylene oxide, and sodium polyacrylate. These water soluble polymers may be used either individually or in combination of two or more thereof. In the case where the water soluble layer is a water soluble nanofiber layer as hereinafter discussed, preferred of these water soluble polymers are pullulan and synthetic polymers, such as partially saponified polyvinyl alcohol, low-saponified polyvinyl alcohol, polyvinylpyrrolidone, and polyethylene oxide, in view of ease of conversion to nanofibers.

The water soluble layer contains a cosmetic component or a medicinal component. As attached to, e.g., human skin, tooth, or gum, the water soluble layer containing such an active ingredient produces the advantageous effect attributed to the active ingredient.

Examples of the cosmetic or medicinal component include a blood circulation improving agent selected from acid mucopolysaccharides, chamomile, buckeye, ginkgo, witch hazel extract, vitamin E, nicotinic acid derivatives, and alkaloid compounds; an edema reducing agent selected from buckeye, flavon derivatives, naphthalenesulfonic acid derivatives, anthocyanin, vitamin P, calendula, concholytic acid, silanol, terminalia, visnaga, and majus; a slimming agent selected from aminophylline, tea extract, caffeine, xanthine derivatives, inositol, dextransulfuric acid derivatives, buckeye, aescin, anthocyanidin, organoiodine compounds, hypericum, Filipendula multijuga, field horsetail, rosemary, ginseng, ivy, thiomucase, and hyaluronidase; a painkiller selected from indometacin, diclofenac, dl-camphor, flurbiprofen, ketoprofen, capsicum extract, piroxicam, felbinac, methyl salicylate, and glycol salicylate; a moisturizing agent selected from polyols, ceramids, and collagens; a peeling agent including a protease; a depilatory agent including calcium thioglycolate; and an autonomic regulatory agent including γ-oryzanol. Additionally, extracts of Japanese elk horn cedar (Thujopsis dolabrata), balloon flower root, eucalyptus, birch, ginger, yuzu (Citrus junos), etc.; tranexamic acid, allantoin, stearyl glycyrrhetinate, niacinamide, l-menthol, and vitamins such as vitamin C are also included in the cosmetic or medicinal component. The content of the active ingredient in the water soluble layer is usually in the range of from 0.01% to 70% by mass, while varying according to the kind.

The active ingredient contained in the water soluble layer is not precluded from being present in the water insoluble nanofiber. However, no particular effect is expected of the presence of the active ingredient in the water insoluble nanofiber. Therefore, the water insoluble nanofiber does not usually have to contain the active ingredient.

The water soluble layer may have a faun selected from (i) a layer of a nanofiber of a water soluble polymer containing the active ingredient (hereinafter also referred to as a water soluble nanofiber layer) and (ii) film or gel of a water soluble polymer containing the active ingredient.

When the water soluble layer has the form (i), the foregoing discussion about the thickness, length, and form (whether solid or hollow) of the water insoluble nanofiber applies to the water soluble nanofiber as well. The thickness of the water soluble layer of the water soluble nanofiber is preferably 100 nm to 1000 μM, more preferably 500 nm to 500 μm, in view of the dissolving properties of the water soluble layer. From the same viewpoint, the water soluble layer of the water soluble nanofiber preferably has a basis weight of 0.01 to 100 g/m$^2$, more preferably 0.1 to 50 g/m$^2$. The thickness of the water soluble layer may be measured using a contact thickness gauge Litematic VL-50A from Mitutoyo Corp. with a spherical carbide contact point of 5 mm in radius.

When the water soluble layer has the form (ii), the water soluble layer which is a water soluble film preferably has a thickness of 1 to 1000 μm, more preferably 5 to 500 μm, in view of the dissolving properties of the water soluble layer. From the same viewpoint, the basis weight of the water soluble layer which is a water soluble film is preferably 0.1 to 100 g/m$^2$, more preferably 1 to 50 g/m$^2$. The water soluble layer which is gel is preferably a water-containing gel with a water content of 20% to 95% by mass. The thickness of the gel is preferably 5 to 1000 μm, more preferably 10 to 500 μm, in view of its water solubility. From the same viewpoint, the gel preferably has a basis weight of 5 to 1000 g/m$^2$, more preferably 10 to 500 g/m$^2$. Whether the water soluble layer is film or gel, the thickness thereof may be measured in the same manner as for the water soluble layer having the form (i).

Figure 1A:
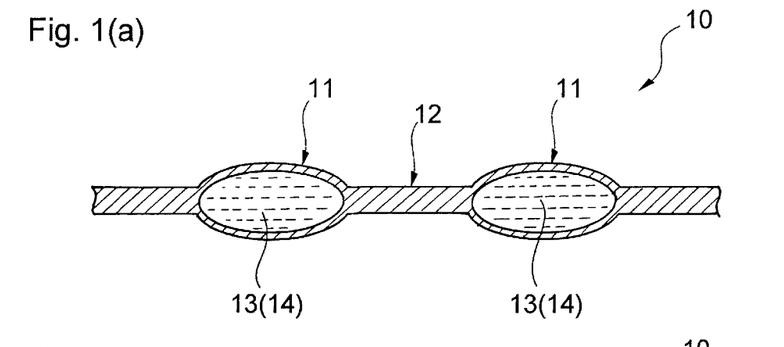
FIG. 1(a), FIG. 1(b), and FIG. 1(c) each represent a schematic cross-sectional structure of a water soluble nanofiber.
Figure 1B:
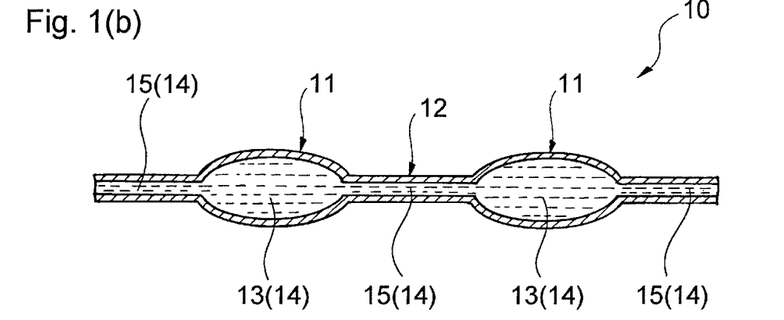
Figure 1C:
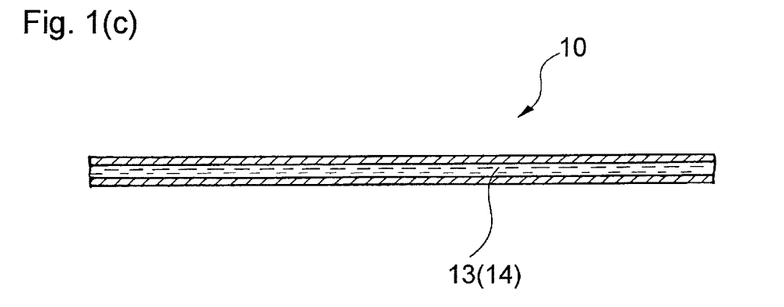

When the water soluble layer has the form (i), the water soluble nanofiber contained in the water soluble layer may have a cavity. The cavity is such that provides a nanospace capable of holding an oily component described later. FIGS. 1(a) through 1(c) each show a cross-section of a nanofiber having a cavity.

The nanofiber 10 shown in FIG. 1(a) has large-diametered portions 11 and small-diametered portions 12 alternating in the extending direction of the nanofiber 10. The large-diametered portion 11 has a cavity 13 having a nanospace inside. As above noted, the cavity 13 holds an oily component 14. On the other hand, the small-diametered portion 12 is solid, having no cavity While in FIG. 1(a) the large-diametered portion 11 and the small-diametered portion 12 are depicted as being almost equal in length in the extending direction of the water soluble nanofiber 10, the length relation between them is not limited thereto. When the water soluble nanofiber 10 of the invention is produced by an electrospinning process described infra, the ratio of the length of the large-diametered portion to that of the small-diametered portion depends on the first liquid to second liquid ratio described infra. While in FIG. 1(a) the large-diametered portion 11 has a generally elliptic cross-section, the cross-sectional shape of the large-diametered portion is not limited thereto. A plurality of the large-diametered portions 11 may be equal or different in cross-sectional shape or thickness. While the small-diametered portion 12 is depicted as being constant in thickness, the thickness may be varied provided that it is smaller than that of the large-diametered portion 11. A plurality of the small-diametered portions 12 may be equal or different in thickness.

Similarly to the nanofiber of FIG. 1(a), the nanofiber 10 shown in FIG. 1(b) has large-diametered portions 11 and small-diametered portions 12. The difference of the nanofiber 10 of this embodiment from the nanofiber of FIG. 1(a) consists in the structure of the small-diametered portions. While the small-diametered portion of the nanofiber 10 of FIG. 1(a) is solid, the small-diametered portion 12 of the nanofiber of the present embodiment is tubular, forming a cavity 15. Similarly to the cavity 13 of the large-diametered portion 11, the cavity 15 of the small-diametered portion 12 holds an oily component 14. The cavity 13 of the large-diametered portion and the cavity 15 of the adjacent small-diametered portion 12 are interconnected. Not every cavity 13 of the large-diametered portion 11 of the nanofiber 10 needs to connect to the cavity 15 of the adjacent small-diametered portion 12.

The nanofiber 10 shown in FIG. 1(c) has no large-diametered portions unlike the nanofibers of FIGS. 1(a) and 1(b). The nanofiber 10 shown has a tubular shape with a substantially constant outer diameter and a substantially constant inner diameter over the whole length thereof, providing a tubular cavity 13 extending over the whole length thereof. The cavity 13 may be continuous or discontinuous over the whole length of the nanofiber 10.

According to each of the above described embodiments shown in FIGS. 1(a) to 1(c), because the nanofiber 10 is capable of retaining an oily component 14 in its cavity 13, it is possible to incorporate the oily component 14 in a high ratio into the nanofiber 10. In particular, the nanofibers 10 of the embodiments shown in FIGS. 1(b) and 1(c) are capable of containing the oily component 14 in a higher ratio because of the cavity 13 extending over the total length thereof. There is substantially no or, if any, very little oily component 14 on the surface of the nanofiber 10. Therefore, it is less likely that an oily component originated in the oily component 14 is present on the surface of the nanofiber 10. That is, even when in using an oily component that is liquid at ambient temperature (5° to 35° C.), the nanofiber 10 is able to contain such an oily component in a high ratio while maintaining a dry feel.

The oily component may be used either alone or in the form of a solution in an organic solvent. Accordingly, the cavity 13 may contain the oily component alone or a solution of the oily component in an organic solvent.

As stated, the nanofiber 10 of the embodiments shown in FIGS. 1(a) to 1(c) is capable of containing an oily component in a higher ratio than conventional nanofibers, preferably in a ratio of 0.5% to 95%, more preferably 10% to 90%, even more preferably 20% to 90%, by mass. The ratio of the water soluble polymer in the nanofiber 10 is preferably 5% to 99.5%, more preferably 10% to 90%, even more preferably 10% to 80%, by mass. The ratios of the water soluble polymer and the oily component in the nanofiber 10 are determined by dissolving a given amount of a nanofiber sheet in water and subjecting the solution to centrifugation.

A variety of oily components are usable in accordance with the intended use of the laminate sheet of the first embodiment. The oily component that can be used for use in, for example, a moisturizing sheet, a cosmetic sheet, or a medical sheet may contain a solvent, such as squalane, olive oil, silicone oil, macadamia nut oil, or cetyl 1,3-dimethylbutyl ether, and an oil-soluble component generally used in cosmetics or for medical use, such as vitamin E, chamomile extract, or rose extract, as dissolved in the solvent as an active ingredient.

The laminate sheet of the first embodiment may be laminated with another sheet. The other sheet that may be used is exemplified by a base sheet that supports the laminate sheet of the first embodiment before use to enhance the handling of the laminate sheet. The combination of the base sheet with the thin laminate sheet of the first embodiment improves the handling in attaching the laminate to skin. The base sheet is preferably disposed on the water insoluble nanofiber layer side of the laminate sheet.

To improve the handling of the laminate sheet of the first embodiment, the base sheet preferably has a Taber stiffness of 0.01 to 0.4 mNm, more preferably 0.01 to 0.2 mNm. The Taber stiffness is measured in accordance with the stiffness testing method specified in JIS P8125.

Beside the Taber stiffness, the thickness of the base sheet can also affect the handling of the laminate sheet of the first embodiment. From this standpoint, the thickness is preferably 5 to 500 μm, more preferably 10 to 300 μm, while varying depending on the material of the base sheet. The thickness of the base sheet can be measured with the contact thickness gauge described supra.

The base sheet is preferably air permeable so as to successfully transfer the laminate sheet of the first embodiment to, e.g., skin. The base sheet preferably has a Gurley air permeance of 30 s/100 ml or less, more preferably 20 s/100 ml or less, as measured in accordance with JIS P8117. The lower limit of the Gurley air permeance is decided taking the Taber stiffness and the like of the base sheet into consideration.

The base sheet is preferably disposed in direct contact with the laminate sheet of the first embodiment. In this case, the base sheet is preferably disposed releasably from the laminate sheet. Such a structure enables to advantage the base sheet to be released from the laminate sheet attached to, e.g., skin, to leave the laminate sheet on the skin.

Useful base sheets include films of synthetic resins, such as polyolefin resins and polyester resins. When such a film is releasably disposed on the laminate sheet, the laminate sheet-facing side of the film is preferably subjected to release treatment, such as application of a silicone resin or a corona discharge treatment, to enhance the releasability.

A mesh sheet is also useful as a base sheet. A mesh sheet can be releasably disposed on the laminate sheet with no particular need to perform the release treatment such as application of a silicone resin or a corona discharge treatment. The mesh sheet preferably has 20 to 200 mesh per inch, more preferably 50 to 150 mesh per inch. The strand diameter of the mesh sheet is preferably 10 to 200 μm, more preferably 30 to 150 μm. The mesh sheet may be of any of the materials of the film described above.

Air-permeable materials such as paper and nonwoven fabric are also useful as a base sheet. Paper or nonwoven fabric can be releasably disposed on the laminate sheet with no particular need to perform the release treatment such as application of a silicone resin or a corona discharge treatment. When the laminate sheet is transferred to skin via a liquid, a paper or nonwoven fabric base sheet will absorb excess water. Materials forming a paper or nonwoven fabric base sheet include naturally occurring fibers, such as plant fibers (e.g., cotton, kapok, wood pulp, non-wood pulp, peanut protein fiber, corn protein fiber, soybean protein fiber, mannan fiber, rubber fiber, hemp, Manila fiber, sisal fiber, New Zealand flax, Luo Buma, coconut, rush, and straw), animal fibers (e.g., wool, goat hair, mohair, cashmere, alpaca, angora, camel, vicuna, silk, plume, down, feather, alginate fiber, chitin fiber, and casein fiber), and mineral fibers (e.g., asbestos); synthetic fibers, such as semisynthetic fibers (e.g., acetate, triacetate, acetate oxide, promix, chlorinated rubber, and hydrochlorinated rubber), metal fibers, carbon fiber, and glass fiber. Also useful are single fibers of a polyolefin, e.g., high density polyethylene, medium density polyethylene, low density polyethylene, or polypropylene, polyester, polyvinylidene chloride, starch, polyvinyl alcohol, or polyvinyl acetate, or a copolymer or modified polymer thereof and core/sheath conjugate fibers having any of these resins as a sheath.

The laminate sheet of the first embodiment is used as attached to, for example, the skin, tooth, or gum of humans, the skin, tooth, or gum of non-human mammals, and the surface of plant parts, such as foliage. The laminate sheet is attached to an object with its water soluble layer facing the surface of the object. The water soluble layer dissolves and disappears with water present on the surface of the object to which it is applied, whereupon the above described active ingredient contained in the water soluble layer is allowed to penetrate into the object to exhibit the expected effect. There remains only the water insoluble nanofiber layer on the object after the disappearance of the water soluble layer. Therefore, when the laminate sheet is used as, for example, a cosmetic sheet, a cosmetic component contained in the water soluble layer penetrates into the skin to exert its skin care effect (e.g., whitening effect or moisturizing effect), and, at the same time, the water insoluble nanofiber layer exerts wrinkle-concealing effect. Moreover, because the uneven texture of the water insoluble nanofiber layer is close to that of human skin, makeup such as foundation may be put on the water insoluble nanofiber layer attached to skin to provide a smooth finish blending with the finish done on the skin.

When the laminate sheet of the first embodiment is used as, for example, an acne-treating sheet, an anti-acne compound is used as an active ingredient. After such an acne-treating sheet is attached to an area of skin having acne, the anti-acne compound contained in the water soluble layer penetrates into the skin to exert its anti-acne effect. Since the water insoluble nanofiber layer remains attached to the skin and overlies the acne, makeup may be put thereon to conceal the acne without adversely affecting the acne. As noted above, putting makeup on the nanofiber layer provides the same finish as done on the skin.

When the laminate sheet of the first embodiment is used as, for example, wound-healing sheet, an anti-inflammatory agent, a bactericidal disinfectant, and the like may be used as the active ingredient. Such a wound-healing sheet, when attached to the wounded part of skin, causes the anti-inflammatory agent, bactericidal disinfectant, etc. contained in the water soluble layer to penetrate into the wound to exert anti-inflammatory or bactericidal disinfectant effect. Since the water insoluble nanofiber layer remains attached to the skin to overlie the wound, the wound is protected by the water insoluble nanofiber layer against bacterial invasion. Additionally, the water insoluble nanofiber layer having air permeability has the effect of preventing the growth of bacteria thereby to prevent the wound from suppurating.

In some applications of the laminate sheet of the first embodiment, the surface of an object to which the laminate sheet is to be attached may be wetted with a liquid before the laminate sheet is applied thereto so that the laminate sheet successfully adheres to the surface of the object with the surface tension taken advantage of. Alternately, the surface of the water soluble layer of the laminate sheet (the side to face the object) may be wetted with a liquid.

The surface of an object may be wetted by, for example, spreading or spraying a liquid of various kinds to the surface. The liquid to be spread or sprayed is preferably a substance containing a component that is liquid at a temperature of attaching the laminate sheet and having a viscosity of about 5000 mPa·s or less at that temperature as measured with a corn-plate rotational viscometer. Such a liquid is exemplified by water, an aqueous liquid, e.g., an aqueous solution or an aqueous dispersion, a nonaqueous solvent, and an aqueous solution or dispersion containing a nonaqueous solvent. Emulsions, including O/W emulsions and W/O emulsions, and liquids thickened with a thickener, such as a thickening polysaccharide, are also useful. More specifically, in the case when the laminate sheet of the first embodiment is used as a cosmetic article to be attached to human skin, a skin lotion or a beauty cream is useful as a liquid wetting the surface of the object (skin).

In place of, or in addition to, the skin lotion or beauty cream, a solid or semisolid pre-makeup primer may be applied to the skin before the laminate sheet is attached. Since a pre-makeup primer smoothes the skin, application of the primer to the skin further enhances the adhesion of the laminate sheet to the skin and the sense of unity of the laminate sheet with the skin.

When the surface of skin or the surface of the laminate sheet is wetted by spreading or spraying a liquid, it suffices that the liquid be applied in a minimum amount required for the liquid to sufficiently exhibit a surface tension. In using an aqueous liquid as the wetting liquid, it suffices that the liquid be applied in a minimum amount enough to sufficiently exhibit a surface tension and to dissolve the water soluble polymer. The amount of the liquid to be applied varies with the size of the nanofiber laminate sheet. For example, in the case of a square laminate sheet measuring 3 cm per side, presence of about 0.01 ml of the liquid on the surface of skin will be enough to attach the laminate sheet to the skin easily. An aqueous liquid, when used as the wetting liquid, will dissolve the water soluble polymer of the laminate sheet to exert a binder effect.

In the case when the laminate sheet of the first embodiment is laminated with the base sheet to provide a base sheet-provided laminate sheet, the base sheet-provided laminate sheet is applied to skin with the laminate sheet side facing the skin, and the base sheet is stripped off to transfer the laminate sheet to the skin. This manner enables a user to successfully attach the laminate sheet, which is less-than-easy to handle due to the low stiffness, to the skin.

In the presence of a liquid between the laminate sheet of the first embodiment and the skin, the bonds between nanofibers are weakened due to the presence of the liquid. In this state, the fiber bonds at the periphery of the laminate sheet may be sheared thereby to smoothen the level difference between the laminate sheet and the skin. As a result, the transition between the laminate sheet and the skin is made less discernible to provide better blending to the eyes between the laminate sheet and the skin. Shearing the fiber bonds at the periphery of the laminate sheet can be achieved by, for example, applying a shear force to the wetted peripheral portion of the laminate sheet attached to the skin. A shear force can be applied by, for example, lightly rubbing or stroking the peripheral portion of the laminate sheet with a finger, a nail, or a makeup tool (e.g., sponge or a cosmetic spatula).

The laminate sheet thus attached and transferred to skin is capable of covering fine skin unevenness, such as lines and pores, to diminish the unevenness and to provide an appearance of fine texture. Besides, the laminate sheet attached to the skin reflects the large unevenness of the skin to which it is attached so that it takes on an extremely natural surface profile and gloss. Such unnaturalness as observed when a thick film, like a silicone film, is attached to skin will hardly be perceived. The laminate sheet which is colored will exert concealing effect on skin tone unevenness due to, e.g., blemishes, freckles, or bags under eyes. The laminate sheet exhibits good adhesion to skin and is thus less likely to lose a sense of unity with the skin during, for example, all-day wear. Having air permeability, the laminate sheet is less likely to impede the regulatory mechanism essentially possessed by skin even when worn for a long period of time. Even after long-time wear, the laminate sheet is easy to remove simply by picking up between fingers.

[Second Embodiment]

While the foregoing embodiment of the invention is of laminate type having a water insoluble nanofiber layer and a water soluble layer, the invention provides, in another embodiment (second embodiment), a nanofiber sheet containing a water insoluble nanofiber and the above described active ingredient-containing water soluble nanofiber. The nanofiber sheet of the second embodiment will then be described. The description relating to the laminate sheet of the first embodiment appropriately applies to the other particulars of the second embodiment not described hereunder. The nanofiber sheet basically has a single-layered structure. The ratio of the water insoluble nanofiber in the nanofiber sheet of the second embodiment is preferably 20% to 90%, more preferably 30% to 90%, by mass, so that the structure of the nanofiber sheet may sufficiently be retained even after the water soluble nanofiber dissolves with water and disappears. On the other hand, the ratio of the water soluble nanofiber is preferably 10% to 80%, more preferably 10% to 70%, by mass, so that a necessary amount of the active ingredient may easily be incorporated into the nanofiber sheet of the second embodiment.

With respect to the ratio of the active ingredient in the water soluble nanofiber, the relevant description about the laminate sheet of the first embodiment applies as appropriate with the term "water soluble layer" being deemed to be replaced with "water soluble nanofiber".

The water insoluble nanofiber may contain other components, typified by a pigment. For example, the water insoluble nanofiber may be colored with a pigment incorporated as described later.

The nanofiber sheet of the second embodiment may have the water insoluble nanofiber and the water soluble nanofiber dispersively mixed uniformly. Alternatively, the nanofiber sheet may have a gradient distribution such that the ratio of the water insoluble nanofiber increases continuously or stepwise from one side to the other with that of the water soluble nanofiber increasing continuously or stepwise in the opposite direction.

The nanofiber sheet of the second embodiment preferably has a basis weight of 0.01 to 100 g/m$^2$, more preferably 0.1 to 50 g/m$^2$, in terms of handling, skin protection, and the like.

When the nanofiber sheet of the second embodiment is attached to the surface of an object, such as the skin, tooth, gum or a like human body part, the water soluble nanofiber in the nanofiber sheet dissolves with water of perspiration or other origin to let the active ingredient in the water soluble nanofiber be absorbed into the body. The water soluble nanofiber completely dissolves and disappears. As a result, only the water insoluble nanofiber remains, retaining the form of thin sheet. This state is similar to the state of the laminate sheet of the first embodiment from which the water soluble layer disappears to leave only the water insoluble nanofiber layer. Accordingly, the nanofiber sheet of the present embodiment produces the same advantageous effects as experienced with the laminate sheet of the first embodiment.

Figure 2:
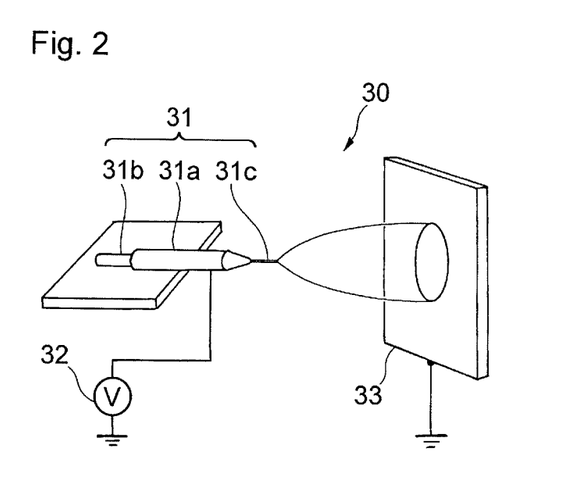
FIG. 2 is a schematic view of an apparatus suited to the production of nanofibers.

A preferred method for producing each of the sheets of the above described embodiments will then be described. In the production of the laminate sheet of the first embodiment, the water insoluble nanofiber layer is suitably produced by, for example, depositing a nanofiber by electrospinning on a smooth surface of a substrate. FIG. 2 illustrates an apparatus 30 for carrying out electrospinning deposition. The apparatus 30 includes a syringe 31, a high voltage supply 32, and a conductive collector 33. The syringe 31 has a cylinder 31$a$, a plunger 31$b$, and a capillary 31$c$. The capillary 31$c$ has an inner diameter of about 10 to 1000 µm. The cylinder 31$a$ is filled with a stock solution for spraying containing a polymer, the raw material of a water insoluble nanofiber. The solvent of the stock solution for spraying may be, for example, an organic solvent such as an alcohol, selected according to the kind of the water insoluble polymer. The high voltage supply 32 is, for example, a 10 to 30 kV direct voltage source. The positive pole of the high voltage supply 32 is electrically connected to the polymer solution in the syringe 31, with the negative pole grounded. The conductive collector 33 is, e.g., a metal plate that is grounded. The distance between the tip of the capillary 31$c$ of the syringe 31 and the conductive collector 33 is set at, e.g., about 30 to 300 mm. The apparatus 30 shown in FIG. 2 may be operated in the atmosphere. The operative environment is not particularly limited and may be, for example, 20° to 40° C. and 10 to 50% RH.

When an aqueous solution of a water insoluble polymer is used as a stock solution for spraying to be electrospun, the stock solution for spraying may be an aqueous solution containing a water soluble polymer that can be rendered water insoluble by a treatment after the formation of a nanofiber. Polyvinyl alcohol is advantageously used as a water soluble polymer that is rendered water insoluble by a treatment after the formation of a nanofiber. Polyvinyl alcohol is water soluble but turns water insoluble on crystallization by heat drying or crosslinking in the presence of a crosslinking agent. A nanofiber obtained by electrospinning an aqueous solution of polyvinyl alcohol may be heated to become a nanofiber of a water insoluble polymer. The heating is preferably carried out at 60° to 200° C. for 1 to 200 minutes.

When in using a polymer that turns water insoluble on heat drying, such a polymer and another water soluble polymer may be dissolved in the same solvent to prepare a stock solution for spraying. The solvent to be used may be water or a mixed solvent of water and a water soluble organic solvent.

Another example of the stock solution for spraying is a solution containing a water soluble polymer, a water insoluble polymer that is soluble in a water-compatible organic solvent, and a mixed solvent of water and the water-compatible organic solvent. Examples of a combination of such an organic solvent and a water insoluble polymer include a combination of oxazoline-modified silicone and ethanol or methanol and a combination of zein and ethanol or acetone.

Still another example of the stock solution for spraying is a solution of (a) a water soluble polymer soluble in both water and an organic solvent and (b) a water insoluble polymer soluble in the organic solvent in (c) the organic solvent. A combination of such a water soluble polymer and such a water insoluble polymer is exemplified by a combination of hydroxypropyl cellulose and polyvinyl butyral.

Any of the above discussed stock solutions for spraying preferably has a total concentration of the polymer(s) of 5% to 35%, more preferably 10% to 25%, by mass.

With a voltage applied between the syringe 31 and the conductive collector 33, the plunger 31$b$ of the syringe 31 is slowly forced into the cylinder 31$a$ to eject the stock solution for spraying from the tip of the capillary 31$c$. The solvent of the extruded stock solution for spraying vaporizes, and the solute (i.e., the polymer) is drawn into a nanofiber while solidifying and attracted onto the conductive collector 33 by the difference in electrical potential. From the principle of the production process, the thus formed nanofiber is a continuous filament of infinite length. A hollow nanofiber is obtained by, for example, using a duplex-tube capillary as the capillary 31c and feeding incompatible solutions in the core and the sheath.

In the case where the water soluble layer of the laminate sheet of the first embodiment is film or gel containing the active ingredient, the film or gel is used as the above described substrate, on which a water insoluble nanofiber is deposited to form a water insoluble nanofiber layer.

In the case where the water soluble layer contains a water soluble nanofiber containing the active ingredient, the water soluble nanofiber containing the active ingredient is deposited by electrospinning onto a separately provided substrate to form a water soluble nanofiber layer, on which a water insoluble nanofiber layer is formed by electrospinning. The order of electrospinning operations may be reversed such that the formation of the water soluble nanofiber layer may be preceded by the formation of the water insoluble nanofiber layer.

Formation of a water insoluble nanofiber layer and a water soluble nanofiber layer may be achieved by, for example, using two syringes. A solution for forming a water insoluble nanofiber layer is ejected from one of the syringes, and thereafter a solution for forming a water soluble nanofiber is ejected from the other syringe. In this case, the resulting laminate sheet exhibits a clear boundary between the composition of the water insoluble nanofiber layer and that of the water soluble nanofiber layer in the laminate sheet thickness direction.

Instead of the above discussed system of ejection, the two syringes may operate simultaneously. A solution for forming a water insoluble nanofiber layer is ejected from one of the syringes at a gradually increasing rate of ejection starting from 0 up to a predetermined rate. A solution for forming a water soluble nanofiber layer is ejected from the other syringe at a gradually decreasing rate of ejection starting from a predetermined rate to zero. According to this ejection system, there is obtained the single-layered nanofiber sheet according to the second embodiment. The resulting single-layered nanofiber sheet has a gradient distribution such that the ratio of the water insoluble nanofiber increases continuously or stepwise from one side to the other with that of the water soluble nanofiber increasing continuously or stepwise in the opposite direction as noted above.

When the two syringes operate simultaneously at respectively constant rates of ejection, there is obtained a single-layered nanofiber sheet in which the water insoluble nanofibers and the water soluble nanofibers are uniformly dispersively mixed.

When nanofibers shown in FIGS. 1(*a*) through 1(*c*) are used as a water soluble nanofiber, electrospinning is carried out as follows. In the case of obtaining the water soluble nanofiber 10 of the embodiment shown in FIG. 1(*a*) or 1(*b*), the stock solution for spraying is prepared by mixing a first liquid and a second liquid. The first liquid is an aqueous solution of a water soluble polymer in water, and the second liquid is an O/W emulsion having an oily component dispersed in an aqueous phase. On mixing the two liquids, an O/W emulsion having the water soluble polymer in the aqueous phase and the oily component in the oily phase is obtained. The thus prepared O/W emulsion is used as a stock solution for spraying to be electrospun to produce the water soluble nanofiber 10 having a desired configuration.

The first liquid preferably has a water soluble polymer concentration of 3% to 30%, more preferably 10% to 25%, by mass, in view of suitable viscosity of the resulting stock solution for spraying. The first liquid is obtained by adding a water soluble polymer to water or an aqueous liquid containing water and a small amount of a water soluble organic solvent and mixing them with or without heating.

The second liquid is obtained by a known emulsifying technique, such as spontaneous emulsification, phase-transfer emulsification, or forced emulsification. The mass ratio of the aqueous phase to the oily phase containing the oily component, aqueous phase/oily phase, is preferably 51:49 to 99:1, more preferably 51:49 to 85:15, to successfully accomplish emulsification. For the same reason, the amount of an emulsifier to be used for emulsification is preferably 0.001% to 20%, more preferably 0.004% to 7%, by mass based on the total mass of the first and the second liquid.

Various surfactants can be used as an emulsifier. Nonionic surfactants, such as a polyethylene glycol monoalkylate, a polyethylene glycol dialkylate, an ethylene glycol dialkylate, and polyoxyethylene hydrogenated castor oil, are particularly preferred for their low irritation to the skin.

When the second liquid is prepared by phase transfer emulsification, an emulsifier is added to an oily phase containing an oily component, followed by heating to a prescribed temperature, and an aqueous phase heated to a prescribed temperature is slowly added thereto while stirring to induce phase transfer to yield an O/W emulsion.

The resulting O/W emulsion (stock solution for spraying) is preferably composed of 55% to 98%, more preferably 60% to 97%, by mass of the aqueous phase and 2% to 45%, more preferably 3% to 40%, by mass of the oily phase.

Electrospinning using the O/W emulsion as a stock solution for spraying results in the formation of the water soluble nanofiber 10 having the structure shown in FIG. 1(*a*) or 1(*b*). This is because, the inventors believe, upon jetting the stock solution for spraying, the phase of the water soluble polymer solution containing much water that is a volatile component tends to exist in the outermost layer, whereas the phase of the oily component undergoing little solvent vaporization tends to exist inside.

Figure 3:
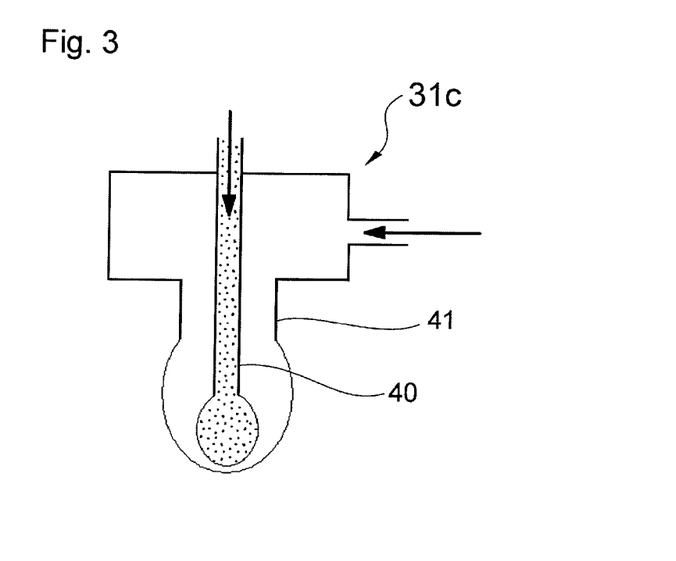
FIG. 3 is an enlarged schematic view showing the structure of a capillary that may be used in the apparatus of FIG. 2.

To produce the water soluble nanofiber 10 having the structure shown in FIG. 1(*c*), a solution of a water soluble polymer in water is used as a first liquid, and an oily component or a solution of an oily component in an organic solvent is used as a second liquid. Electrospinning is carried out using the apparatus of FIG. 2 in which the capillary 31c is a duplex-tube capillary having an inner cylinder 40 and an outer cylinder 41 as shown in FIG. 3. The second liquid is fed to the core, and the first liquid is fed to the sheath. A nanofiber having the structure as designed is obtained successfully by properly balancing the amounts of the first and the second liquid to be ejected.

The subject matter common to the above discussed two embodiments, i.e., the nanofiber laminate sheet of the first embodiment and the nanofiber sheet of the second embodiment, will then be described. In the following description, the nanofiber laminate sheet of the first embodiment and the nanofiber sheet of the second embodiment will be inclusively referred to as the "nanofiber sheet of the invention" for the sake of simplicity. It will be understood that the "nanofiber sheet of the invention" means either one or both of the nanofiber laminate sheet of the first embodiment and the nanofiber sheet of the second embodiment according to the context in which it appears.

Subject Matter-1 Common to the First and the Second Embodiment:

The water insoluble nanofiber may contain a coloring pigment. The water insoluble nanofiber containing a coloring pigment, the nanofiber sheet of the invention has a coloration resulting from the coloring pigment. As used herein, the term "coloration" or "coloring" is a concept inclusive of both chromatic and achromatic colors including a white color. The nanofiber sheet of the invention which contains a coloring pigment-containing water insoluble nanofiber is a thin sheet and is suited for use as a cosmetic sheet for makeup that is attached directly to the skin of a user to do makeup.

When the nanofiber sheet of the invention is used as a cosmetic sheet that is attached directly to the skin of a user to exert cosmetic effect, particularly as a cosmetic sheet for makeup, the nanofiber sheet of the invention may be colored in a color complementary to human skin color or its vicinity that corrects the human skin tone, e.g., yellow, blue to green, purple, brown, and the like. To allow for better blending with the surrounding skin, the nanofiber sheet of the invention is advantageously colored in a color close to skin tone. In order for the nanofiber sheet of the invention attached to skin to effectively conceal skin color unevenness (e.g., blemishes, freckles, or bags under eyes), it is particularly advantageous for the nanofiber sheet to be colored in skin tone. For all these considerations, the nanofiber sheet preferably has in its dry state an outer color with a hue of 5.0 R to 9.8 YR (red through orange to yellow), a value of 5.0 to 8.0, and a chroma of 2.5 to 6.0 in the Munsell color system, more preferably a hue of 2.0 YR to 9.0 RY, a value of 5.2 to 7.8, and a chroma of 2.7 to 5.8. These attributes are measured using commercially available colorimetric equipment, such as a chroma meter CR-400 or a spectrophotometer CM-700d both from Konica Minolta Sensing Inc. The outer color of the sheet is measured with the sheet placed on black paper with a hue of 7.7Y, a value of 2.6, and a chroma of 0.3.

In order for the nanofiber sheet of the invention to have the above specified outer color, it is preferred to use two or more coloring pigments different in hue to be incorporated into the water insoluble nanofiber constructing the nanofiber sheet. For example, a combination of red, yellow, and black is usually used for skin tone correction. The combination may further be combined with blue or white.

Examples of useful white pigments include titanium oxide and zinc oxide. Coloring pigments other than white pigments include inorganic pigments, such as yellow iron oxide, red iron oxide, black iron oxide, carbon black, ultramarine blue, Prussian blue, blue titanium oxide, black titanium oxide, chromium oxide, chromium hydroxide, and a titanium/titanium oxide sintered product; organic pigments, such as Red No. 201, Red No. 202, Red No. 226, Yellow No. 401, and Blue No. 404; lake pigments, such as Red No. 104, Red. No. 230, Yellow No. 4, Yellow No. 5, and Blue No. 1; and organic pigments coated with polymers, such as a polymethacrylic ester. Pearlescent pigments are also useful, including inorganic particles, such as titanium oxide-coated mica (titanated mica), red iron oxide-coated mica, bismuth oxychloride, titanium oxide-coated bismuth oxychloride, iron oxide-coated titanated mica, organic pigment-coated titanated mica, silicic acid titanium-treated mica, titanium oxide-coated talc, silicon dioxide red iron oxide-treated aluminum, and titanium oxide-coated glass powder; and flaky aluminum particles coated with an organic resin (e.g., polyethylene terephthalate). The coloring pigment may be surface-treated to have improved dispersibility. Examples of suitable surface treatment include hydrophobilization using a hydrophobilizing agent of various kinds generally applied to cosmetic particles, such as silicone treatment, fatty acid treatment, lauroyl lysine treatment, surfactant treatment, metal soap treatment, fluorine compound treatment, lecithin treatment, nylon treatment, and polymer treatment.

The size of the coloring pigment incorporated into the water insoluble nanofiber is usually almost equal to or smaller than the thickness of the water insoluble nanofiber, or larger than the thickness of the water insoluble nanofiber. When the size of the coloring pigment is almost equal to or smaller than the thickness of the water insoluble nanofiber, the nanofiber sheet of the invention is able to reduce color unevenness even with a small thickness. When the coloring pigment is larger than the thickness of the water insoluble nanofiber, the unevenness due to the particulate coloring pigment is reflected on the surface of the water insoluble nanofiber. The surface of the water insoluble nanofiber therefore reflects light diffusely because of its surface unevenness. The diffuse reflection makes the visual effects of the nanofiber sheet of the invention more pronounced.

The size of the coloring pigment in terms of average particle size is preferably 10 to 1000 nm, more preferably 50 to 900 nm. The thickness of the water insoluble nanofiber being within the above recited range, the average particle size of the coloring particles preferably falls within a range of from 20% to 95%, more preferably from 30% to 90%, of the thickness of the nanofiber. With the average particle size of the coloring particles being in that range, the particulate coloring pigment is covered within the water insoluble nanofiber so that agglomeration of the coloring particles is prevented, that the resulting sheet of the coloring particle-containing water insoluble nanofiber has reduced color unevenness even with a small thickness, and that the sheet can be wetted with a small amount of a liquid when attached to skin. The average particle size is measured with, for example, a laser diffraction particle size distribution analyzer. The amount of the coloring pigment to be incorporated into the water insoluble nanofiber, while varying according to the kind, is preferably 1% to 50%, more preferably 15% to 40%, by mass relative to the water insoluble nanofiber to exhibit sufficient tinctorial strength. In using an organic pigment or a lake pigment as a coloring pigment with which the nanofiber sheet is ready to be colored, a small amount of about 1% to 10% by mass of the coloring pigment will be enough to produce a uniformly colored nanofiber sheet free of color unevenness. The amount of a coloring pigment present in a water insoluble nanofiber is measured by immersing the water insoluble nanofiber in a solvent capable of dissolving the insoluble nanofiber to cause the nanofiber to dissolve therein, if necessary with the aid of a mechanical force, e.g., of an ultrasonic cleaner, repeatedly subjecting the solid matter to washing and filtration, drying finally collected solid, and weighing the dried solid using, e.g., a balance.

A pigment with a particle size exceeding 1000 nm may be used as a coloring pigment in combination with a small-sized (1000 nm or smaller) pigment. Some of while pigments (e.g., platy titanium oxide or zinc oxide) and pearlescent pigments have a particle size exceeding 1000 nm. Such pigments have a function to increase diffuse transmission thereby to gradate the border of the shade underneath the nanofiber sheet of the invention and make the border less visible or a function to suppress reflection on the surface of the nanofiber sheet of the invention thereby to reduce the difference in light brightness as well as the coloring function. Thus, a combined use of such pigment particles enhances the color unevenness reducing effect or the effect of making fine unevenness less discernible.

After the nanofiber sheet of the invention containing the coloring pigment-containing water insoluble nanofiber is attached to, e.g., skin, makeup may be put on the nanofiber sheet thereby to provide better visual blending of the nanofiber sheet with the skin. Makeup cosmetics that may be put on include an oil and an emulsion containing the oil. The oil or the oil of the emulsion applied to the nanofiber sheet will be retained in interfiber spaces of the nanofiber sheet, which will provide better visual blending with the skin. The oil to be used preferably has a viscosity of 5.5 to 100 mPa·s at ambient temperature (25° C.). In particular, polydimethylsiloxane (silicone oil) is preferred to a hydrocarbon oil in terms of makeup longevity.

Various powdery cosmetics typified by powder foundation may be put on the nanofiber sheet attached to skin with or without the oil or the oil-containing emulsion applied to the nanofiber sheet. By virtue of the nanofiber thickness and interfiber distance of the nanofiber sheet, powdery makeup goes on evenly and smoothly on the nanofiber sheet and will give improved visual blending with the similarly made-up skin.

The water insoluble nanofiber containing a coloring pigment is suitably made by, for example, electrospinning. Electrospinning can be carried out in the same manner as previously described, provided that the stock solution for spraying contains the nanofiber-forming polymer and a coloring pigment. The solvent of the stock solution for spraying is selected from water, an organic solvent, and a mixed solvent of water and a water-compatible organic solvent according to the polymer and the coloring pigment to be used.

On ejecting the stock solution for spraying from the tip of the capillary 31c (FIG. 2) in electrospinning, the solvent of the stock solution for spraying vaporizes, and the solute (i.e., the polymer) is drawn into a nanofiber while solidifying and attracted onto the conductive collector 33 by the difference in electrical potential. The coloring pigment contained in the stock solution for spraying is taken into the polymer being solidified.

As stated, the stock solution for spraying used in electrospinning contains a polymer and a coloring pigment. The stock solution for spraying may be prepared by mixing the polymer, the coloring pigment, and a liquid medium. According to this preparation method, however, the coloring pigment is liable to settle out in the stock solution for spraying on account of its high agglomerating tendency. An agglomerated coloring pigment causes clogging of the capillary 31c of the apparatus and generation of color unevenness and spots of agglomerates in the resulting nanofiber sheet. It is then preferred in the invention that the stock solution for spraying be prepared by mixing (i) a slurry containing the coloring pigment and (ii) a solution containing the polymer. The coloring pigment exhibits good dispersibility in the thus prepared stock solution for spraying to provide a uniformly colored nanofiber, and clogging of the capillary 31c is less likely to occur. The preferred method for preparing the stock solution for spraying will further be described below.

The slurry (i) is prepared by dispersing a coloring pigment in a liquid medium. The liquid medium is chosen as appropriate to the coloring pigment. A volatile liquid medium is especially preferred; for the liquid component will easily be removed during the nanofiber formation by electrospinning. From this viewpoint, water or an organic solvent is a preferred liquid medium. Examples of the organic solvent include acetone, isoparaffin, ethanol, and silicone compounds, such as cyclomethicones, e.g., octamethylcyclotetrasiloxane and decamethylcyclopentasiloxane, dimethicones, e.g., octamethyltrisiloxane and dodecamethylpentasiloxane, and methyltrimethicone. More preferred are silicone compounds for their safety to skin.

The ratio of the coloring pigment in the slurry is preferably 5% to 50%, more preferably 10% to 40%, by mass, to achieve a good balance between coloring effect and quality uniformity of the nanofiber sheet. With at least 5% by mass of the coloring pigment in the slurry, a sufficient coloring effect on the sheet is produced. With the ratio of the pigment being 50% by mass or less, the pigment is dispersed well to effectively prevent reduction in quality of the nanofiber sheet due to agglomeration of the pigment particles. Two or more coloring pigments may be used in combination according to the desired color of the nanofiber. The coloring pigment is preferably previously ground to a prescribed size to have a controlled particle size before preparation of the slurry. The coloring pigment may or may not be subjected to surface treatment commonly conducted in the preparation of cosmetics.

The slurry may contain, in addition to the coloring pigment, a dispersant for improving the dispersibility of the coloring pigment or a defoaming agent for preventing the slurry from foaming. The ratio of the dispersant in the slurry is preferably 10% or less, more preferably 0.1% to 10%, even more preferably 1% to 6%, by mass, so as to sufficiently improve the dispersibility of the coloring pigment. The ratio of the defoaming agent in the slurry is preferably 2% or less, more preferably 0.01% to 1.5%, even more preferably 0.1% to 0.5%, by mass, to prevent the slurry from foaming.

Various kinds of surfactants may be used as a dispersant, for example. Nonionic surfactants or anionic surfactants are particularly preferred. These surfactants may be used either individually or in combination of two or more thereof. In the latter case, the total amount of the surfactants is preferably in the range recited above. Examples of useful surfactants include fatty acid metal salts, alkylsulfates, alkyl ether sulfates, alkylphosphates, and alkyl ether phosphates. Specific examples include anionic surfactants, such as sodium laurylsulfate, sodium polyoxyethylene lauryl ether sulfate, sodium polyoxyethylene lauryl ether phosphate, and sodium polyoxyethylene oleyl ether phosphate; polyethylene alkyl ethers, such as polyoxyethylene octyl dodecyl ether, glycerol fatty acid esters, propylene glycol fatty acid esters, sorbitan fatty acid esters, sucrose fatty acid esters, fatty acid mono(di) ethanolamides, polyethylene glycol fatty acid esters, polyoxyethylene sorbitol fatty acid esters, and polyoxyethylene hydrogenated castor oil. Specific examples of nonionic surfactants include glycerol monostearate, sorbitan sesquioleate, sucrose fatty acid esters, coconut oil fatty acid diethanolamide, polyethylene glycol monostearate, polyethylene glycol monooleate, polyoxyethylene lauryl ether, polyoxyethylene stearyl ether, polyoxyethylene oleyl ether, polyoxyethylene glycerol monostearate, polyoxyethylene sorbitan monostearate, polyoxyethylene sorbitol tetraoleate, and polyoxyethylene hydrogenated castor oil.

The defoaming agent is preferably a silicone defoaming agent, such as dimethylsilicone oil, silicone oil compounds, silicone emulsions, polyether-modified polysiloxane, and fluorosilicone oils.

The components above described are mixed with a liquid medium, such as water or an organic solvent, and dispersed in a dispersing machine while grinding the coloring pigment. Examples of a useful dispersing machine include media mills, such as a ball mill and a bead mill, and a disper.

Two or more slurries having different coloring pigment formulations may be prepared so that two or more of such slurries may be used in an appropriate ratio according to the desired nanofiber color. For example, a slurry containing only a white pigment (hereinafter referred to as a white slurry) and one or more slurries each containing one or more pigments other than white (hereinafter referred to non-white slurries) may be provided. In terms of higher freedom of color matching, it is preferred to prepare a stock solution for spraying to be electrospun by mixing the white slurry, one or more non-white slurries, and a polymer solution. For instance, when a nanofiber sheet colored in skin tone is desired, a white slurry and a brown slurry as a non-white slurry may be used in combination.

The polymer solution (ii) that is used in combination with the coloring pigment slurry (i) is selected as appropriate to the polymer or the coloring pigment slurry. For example, a polymer solution that is to be mixed with a coloring pigment slurry having an organic solvent as a medium is preferably a solution of a polymer in an organic solvent compatible with the organic solvent of the slurry.

In mixing the coloring pigment slurry (i) and the polymer solution (ii) to prepare a stock solution for spraying to be electrospun, the ratio of the polymer solution (ii) in the stock solution for spraying is preferably 40% to 80%, more preferably 50% to 70%, by mass, and that of the coloring pigment slurry (i) is preferably 20% to 60%, more preferably 30% to 50%, by mass.

Figure 4A:
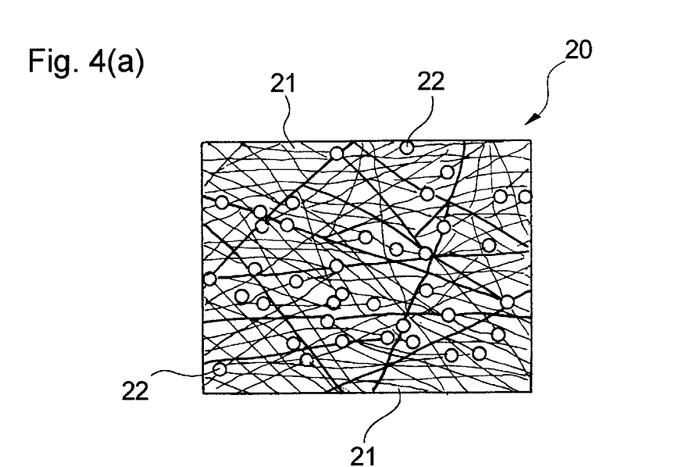
FIG. 4(a) schematically illustrates the structure of a water insoluble nanofiber sheet.
Figure 4B:
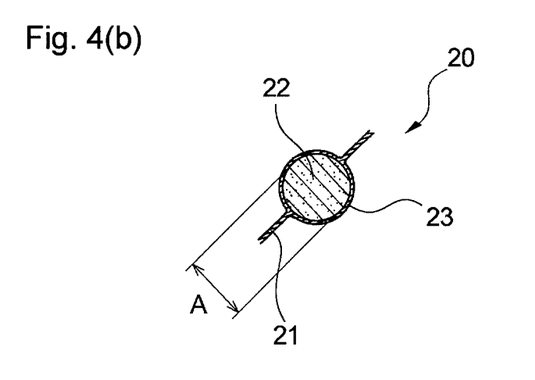
FIG. 4(b) is an enlarged view of an essential part of FIG. 4(a).

Subject Matter-2 Common to the First and the Second Embodiment:

The water insoluble nanofiber may be a water insoluble composite nanofiber 20 composed of a water insoluble nanofiber and a particle fixed thereto as shown in FIGS. 4(a) and 4(b). In detail, a composite is formed of a water insoluble nanofiber 21 having a particle 22 fixed thereto as shown in FIG. 4(a). One nanofiber has one or more particles fixed thereto. One of the features of the composite nanofiber is the relation between the nanofiber thickness and the size of the particle. In more detail, the particle has a particle size A greater than the thickness B of the nanofiber as shown in FIG. 4(b). The nanofiber sheet containing the composite nanofibers have the following advantages resulting from such a relation. On applying the nanofiber sheet to, for example, human skin, the particle enters a depression of the skin surface, such as a line and a pore. When the skin is deformed due to contraction, the particle having entered the depression acts to hinder the deformation, whereby a line or a wrinkle hardly forms, and the skin unevenness becomes less noticeable. Furthermore, the presence of the particle greater than the nanofiber thickness creates unevenness on the nanofiber sheet surface, which enhances light scattering and thereby improves the texture of the nanofiber sheet. The unevenness on the nanofiber sheet surface is also advantageous for makeup cosmetics such as foundation to go on smoothly. Accordingly, the nanofiber sheet containing the composite nanofiber is specially suited for use as a skin unevenness-concealing sheet that is used as attached to human skin for beauty. To ensure the inhibitory effect on wrinkle formation, the particle size is preferably 1 to 150 µm, more preferably 1 to 100 µm, even more preferably 3 to 50 µm, provided that it is greater than the nanofiber thickness. The nanofiber thickness is preferably 10 to 3000 nm, more preferably 10 to 1000 nm.

The particle size A of the particle 22 may be measured in a wet system using a laser diffraction particle size distribution analyzer, SALD-300V from Shimadzu Corp. The median diameter of the particles thus measured is taken as the particle size A.

To make the nanofiber sheet attached to human skin as less discernible as possible, it is desirable that the thickness B of the nanofiber be as small as possible. However, too thin nanofibers have difficulty in holding the large diameter particles. For these considerations, it is preferred for the thickness B to be in the range recited above. The ratio of the particle size A to the nanofiber thickness B, A/B, is preferably 1.1 to 200, more preferably 5 to 100, for allowing the nanofiber to certainly hold the particle.

The way a particle is fixed to the nanofiber is another feature of the composite nanofiber. In detail, as shown in FIG. 4(b), the particle 22 is covered with the material 23 constituting the nanofiber 21 in the composite nanofiber 20. The material 23 functions as a binder between the particle 22 and the nanofiber 21, whereby the particle 22 is certainly held to the nanofiber 21. To make it more certain that the particle 22 is held to the nanofiber 21, it is desirable that the composite nanofiber 20 have the particle 22 covered completely with the material 23 constituting the nanofiber 21, but it is not essential for the particle 22 to be completely covered.

As stated earlier, the particle fixed to the nanofiber enters the depression of human skin such as a wrinkle and prevents the wrinkle from getting deeper. From this standpoint, the particle preferably has such a shape that prevents skin from getting a wrinkle. As a result of the inventors' study, platy particles were revealed to be effective in preventing getting wrinkles.

The platy particles may have a polygonal (e.g., circular, elliptic, triangular, rectangular, or hexagonal) or an amorphous main face. The platy particles preferably have an aspect ratio (diameter/thickness) of 1.5 to 10000, more preferably 2 to 1000.

The particle size of the platy particles may be measured in a wet system using a laser diffraction particle size distribution analyzer, SALD-300V from Shimadzu Corp. The median diameter of the particles thus measured is taken as the particle size.

Examples of the platy particles include talc and mica. Clay minerals, such as kaolinite, montmorillonite, and illite, are also useful. Platy particles of a sintered metal oxide, such as alumina and of an inorganic compound, such as calcium carbonate, are also useful. These platy particles may be used either individually or in combination of two or more kinds thereof.

In addition to the above described platy particles, light scattering particles are also useful as a particle to be attached to the nanofiber. Because such particles having entered a depression of skin, such as a wrinkle, scatter light, the wrinkle will be made less discernible. As used herein, the term "light scattering" means a function to increase diffuse transmission thereby to gradate the border of the shade underneath the nanofiber sheet of the invention and make the border less discernible or a function to suppress reflection on the surface of the nanofiber sheet of the invention thereby to reduce the difference in light brightness.

Examples of useful light-scattering particles include granular barium sulfate, alumina, or aluminum hydroxide; finely textured platy particles of mica and the like; spherical particles of polymers, such as silicone resins, polyamide, and polymethyl methacrylate; and composite powders. These particles may be used either alone or in combination of two or more thereof. Preferred of them are spherical particles of polymers, such as polyamide and polymethyl methacrylate, and composite powders; for they will provide a sheet with regular unevenness that may be regarded as a heterogeneous film showing a continuously varying refractive index. The light scattering particles may be platy but do not need to be platy unlike the above discussed platy particles.

The platy particles and the light scattering particles may be used either individually or in an appropriate combination thereof.

The amount of the large diameter particles fixed to the nanofibers is preferably 1% to 70%, more preferably 5% to 60%, by mass relative to the mass of the composite nanofibers. With that amount, the nanofiber forms stably, and the large diameter particles are uniformly distributed in the nanofiber sheet.

The composite nanofiber may further contain small diameter particles having a smaller particle size than the nanofiber thickness in addition to the large diameter particles. The small diameter particles are used primarily for the nanofiber and incorporated into the nanofiber for the purpose of, for example, coloring the nanofiber. The details of the small diameter coloring pigment are as previously described. Specifically, pigments and metal particles with a particle size of about 10 to 1000 nm are useful. The ratio of the small diameter coloring pigment in the composite nanofiber is preferably 50% or less, more preferably 10% to 40%, by mass. When the nanofiber sheet is used as attached to human skin for the purpose of beauty, a pigment of skin tone is preferably used as the small diameter particles. The term "pigment of skin tone" is intended to mean a pigment having a hue of 2.0 YR to 9.0 RY, a value of 5.2 to 8.0, and a chroma of 2.7 to 4.7 in the Munsell color system.

The nanofiber sheet of the invention containing the composite nanofiber is especially suited for use as an unevenness-concealing sheet for beauty that is to be attached to human skin.

The composite nanofiber is produced by electrospinning using the above described apparatus shown in FIG. 2. The inner diameter of the capillary 31C shown in FIG. 2 is about 400 to 1200 μm and is set to be larger than the particle size of the large diameter particle to be fixed to the nanofiber. The stock solution for spraying to be electrospun preferably contains the polymer in a concentration of 3% to 50% by mass and the large diameter particles in a concentration of 2% to 30% by mass.

Subject Matter-3 Common to the First and the Second Embodiment:

The water insoluble nanofiber and/or the water soluble nanofiber in the nanofiber laminate sheet of the first embodiment and the nanofiber sheet of the second embodiment may contain a volatile functional agent. The volatile functional agent is preferably at least one member selected from the group consisting of a fragrance, a whitening agent, and a taste corrector. As used herein, the "fragrance" means a substance capable of imparting a pleasant scent to air at ambient temperature and atmospheric pressure and having a "fragrant function". As used herein, the "whitening agent" means a substance which is, when applied to a human body part, capable of whitening the part or maintaining the part in a youthful and healthy condition and has a "whitening function". As sued herein, the "taste corrector" means a substance capable of changing or diminishing a taste and having a "taste correcting function". For example, a taste corrector may change bitterness or sourness to another taste, e.g., sweetness, or reducing a taste. These functional agents are volatile substances vaporizing at ambient temperature and atmospheric pressure. As used herein, the term "ambient temperature and atmospheric pressure" usually means a condition of a temperature of 23° C. and an atmospheric pressure of 101.325 kPa.

The volatile functional agent preferably has a vapor pressure at 20° C. of 13.3 Pa or less, more preferably 0.0013 to 10.7 Pa, even more preferably 0.0133 to 6.7 Pa. With the vapor pressure at 20° C. of the volatile functional agent falling within that range, the nanofiber sheet of the invention containing the volatile functional agent-containing nanofiber will exhibit a useful function attributed to the volatile functional agent at ambient temperature and atmospheric pressure. For instance, a nanofiber sheet containing a nanofiber containing a fragrance as a volatile functional agent is a fragranced sheet capable of releasing a fragrance into air at ambient temperature and atmospheric pressure thereby to make a user feel exhilarated, refreshed, cleaned, or relaxed and also produce a deodorizing effect, an anesthetic (analgesic) effect, or a like effect.

When the nanofiber is produced by electrospinning in a usual manner using a stock polymer solution containing a volatile functional agent whose vapor pressure at 20° C. exceeds 13.3 Pa (hereinafter also referred to as an easily volatile functional agent), the easily volatile functional agent tends to vaporize during the electrospinning because of its high volatility. It can follow that the resulting nanofiber fails to retain a sufficient amount of the easily volatile functional agent for performing the function expected of the use of the easily volatile functional agent, for example, a fragrant function of an easily volatile fragrance. Nevertheless, it is possible to impart the function of such an easily volatile functional agent to a nanofiber sheet by timely adding the easily volatile functional agent, as will be described later. The vapor pressure of a volatile functional agent is obtained from the data base provided by Research Institute for Fragrance Materials (RFIM).

Examples of fragrances that can be used as a volatile functional agent include vanillin, methyl jasmonate, γ-undecalactone, and phenylethyl alcohol. These volatile functional agents may be used either individually or in combination of two or more thereof.

The volatile functional agent content in the nanofiber is preferably 0.001% to 30%, more preferably 0.01% to 5%, by mass. The recited range of the volatile functional agent content assures production of a nanofiber sheet performing a useful function of the volatile functional agent, such as fragrance release, and achieves reduction in the amount of the volatile functional agent to be used, leading to a reduced cost of production.

In using a volatile functional agent whose vapor pressure at 20° C. is 13.3 Pa or less, volatilization of the volatile functional agent during the electrospinning process is effectively avoided. On the other hand, in the case when an easily volatile functional agent is used, the following method A or B enables the function of the easily volatile functional agent to be successfully imparted to a nanofiber sheet.

Method A: A method for producing a nanofiber sheet including a step of making a nanofiber of a polymer (nanofiber making step) and a step of applying a solution containing an easily volatile functional agent to the nanofiber (solution addition step).

Method B: A method for producing a nanofiber sheet including a step of making a nanofiber of a polymer (nanofiber making step) and a step of leaving an easily volatile functional agent to stand close to the nanofiber layer for a prescribed period of time (easily volatile functional agent transfer step).

The nanofiber making step in the methods A and B is carried out by electrospinning using the apparatus shown in FIG. 2.

The solution containing an easily volatile functional agent for use in the solution addition step of the method A is prepared by dissolving or dispersing the easily volatile component in a solvent. The solvent is preferably uninfluential on the nanofiber and is chosen from, for example, water, an organic solvent, and a mixed solvent of water and a water-compatible organic solvent. Application of the solution containing the easily volatile functional agent to the nanofiber may be achieved by, for example, spraying the solution to the nanofiber or immersing the nanofiber sheet in the solution.

The easily volatile functional agent transfer step of the method B is a step in which the nanofiber and the easily volatile functional agent are brought close to but not in contact with each other thereby to cause the vapor of the easily volatile functional agent to transfer to the nanofiber. If the nanofiber and the easily volatile functional agent are brought into contact with each other, the polymer constituting the nanofiber can dissolve or swell to lose its fibrous form. The easily volatile functional agent placed close to the nanofiber may be exposed to open air or be enclosed in an air permeable bag or a like enclosure. Unintentional direct contact of the nanofiber with the easily volatile functional agent is certainly avoided by enclosing the easily volatile functional agent. The period of time that the easily volatile functional agent is left to stand close to the nanofiber is decided as appropriate to the type of the easily volatile functional agent and the like. In general, the higher the volatility of the functional agent, the shorter the time needed.

While the invention has been described with reference to its preferred embodiments, it should be understood that the invention is not limited to these embodiments. For example, while the method for producing the nanofiber has been described with particular reference to electrospinning deposition, the method for producing the nanofiber is not limited thereto.

While, according to the electrospinning technique shown in FIG. 2, the nanofiber formed is deposited on the conductive collector 33 of plate shape, a conductive rotating drum may be used instead of the plate-shaped collector, in which case the nanofiber is deposited on the peripheral surface of the rotating drum.

EXAMPLES

The invention will now be illustrated in greater detail by way of Examples, but it should be understood that the scope of the invention is not limited thereto. Unless otherwise noted, all the percentages are by mass.

Example 1

Polyvinyl butyral BM-1 available from Sekisui Chemical Co., Ltd. was used as a water insoluble compound. BM-1 was dissolved in an aqueous ethanol solution in a concentration of 15% to make a stock solution for spraying for electrospinning. The stock solution for spraying was electrospun by the use of the apparatus shown in FIG. 2 in which polyethylene terephthalate mesh (bolting cloth, Tetron T-No. 100T, from Tokyo Screen Co., Ltd.) was placed on the surface of the collector 33, to form a water insoluble nanofiber layer having a basis weight of 5 $g/m^2$ on the mesh. The electrospinning conditions are described below.
Applied voltage: 26 kV
Capillary-collector distance: 120 mm
Rate of ejection of aqueous solution: 1.0 ml/hr
Environment: 26° C., 40% RH Pullulan available from Hayashibara Shoji Inc. was used as a water soluble compound. Pullulan was dissolved in 80° C. water to make a 15% aqueous solution. The solution was cooled to ambient temperature, and ascorbic acid was dissolved therein in a concentration of 5% to prepare a stock solution for spraying to be electrospun. The stock solution for spraying was electrospun onto the surface of the above prepared water insoluble nanofiber layer to form a water soluble nanofiber layer having a basis weight of 5 $g/m^2$. The resulting nanofiber laminate sheet had a total basis weight of 10 $g/m^2$. The electrospinning conditions are described below.
Applied voltage: 25 kV
Capillary-collector distance: 185 mm
Rate of ejection: 1.0 ml/hr
Environment: 26° C., 40% RH There was thus obtained a laminate sheet composed of one water insoluble nanofiber layer and one water soluble nanofiber layer.

Example 2

A laminate sheet was obtained in the same manner as in Example 1, except that a skin tone pigment was compounded into the polyvinyl butyral solution in a concentration of 2.9%. The resulting nanofiber sheet had a color with a hue of 7.6YR, a value of 7.8, and a chroma of 4.3.

Example 3

A film of pullulan containing 5% ascorbic acid and having a basis weight of 20 $g/m^2$ was prepared. A laminate sheet having one water insoluble nanofiber layer and one water soluble film was obtained in the same manner as in Example 1, except that the water soluble nanofiber layer in Example 1 was replaced with this film, on which the water insoluble nanofiber layer was deposited.

Example 4

The water insoluble compound solution and the water soluble compound solution used in Example 1 were simultaneously fed to the respective syringes at the same rate and electrospun to form a nanofiber sheet having a basis weight of 20 $g/m^2$. The electrospinning conditions were as follows.
Applied voltage: 25 kV
Capillary-collector distance: 120 mm
Rate of ejection: 1.0 ml/hr
Environment: 26° C., 40% RH Comparative Example 1

The water insoluble compound solution used in Example 1 was processed to prepare a polyvinyl butyral cast film with a thickness of 18 μm and a basis weight of 20 $g/m^2$. The same procedure as in Example 1 was followed, except for using the resulting cast film, to produce a laminate sheet composed of the polyvinyl butyral cast film and the water soluble nanofiber.

Comparative Example 2

The same procedure as in Example 1 was followed, except for using polypropylene melt-blown nonwoven fabric (PC0020 from Kuraray Co., Ltd.; basis weight: 20 $g/m^2$) as a water insoluble layer, to produce a laminate sheet composed of the melt-blown nonwoven fabric and the water soluble nanofiber.

Evaluation:

The sheets obtained in Examples and Comparative Examples were evaluated for adhesion to human skin in accordance with the following test method. The subjects (n=3) were of both sexes, aged 25 to 40. The inner side of a forearm of each subject was washed using a neutral surfactant, wiped with waste cloth to remove water drops, and allowed to stand at 23° C. and 50% RH for a sufficient time to stabilize the skin surface. Thereafter, a 70 mm diameter area of the skin was uniformly misted with 0.05 g of ion exchanged water, and each of the sheets obtained in Examples 1 to 4 and Comparative Examples 1 and 2 cut to 20 mm by 20 mm was attached to the wetted skin and allowed to stand until water dried. After 60 minutes, the adhesion of the sheet to the skin was rated as follows.

Good: The nanofiber sheet remains attached to the skin even at the four corners.

Poor: The nanofiber sheet peels for the most part.

TABLE 1

|  |  | Example 1 | Example 2 | Example 3 | Example 4*[1] | Compara. Example 1 | Compara. Example 2 |
|---|---|---|---|---|---|---|---|
| Water Insoluble Component | Kind | PVB nanofiber layer | pigment-contg. PVB nanofiber layer | PVB nanofiber layer | PVB nanofiber | PVB film | melt-blown nonwoven fabric |
|  | Thickness (nm) | 500 | 550 | 500 | 500 | — | 5000 |
|  | Basis Weight (g/m$^2$) | 5 | 5 | 5 | — | 20 | 20 |
| Water Soluble Component | Kind | ascorbic acid-contg. pullulan nanofiber layer | ascorbic acid-contg. pullulan nanofiber layer | ascorbic acid-contg. pullulan film | ascorbic acid-contg. pullulan nanofiber | ascorbic acid-contg. pullulan nanofiber layer | ascorbic acid-contg. pullulan nanofiber layer |
|  | Thickness (nm) | 410 | 410 | — | 410 | 410 | 410 |
|  | Basis Weight (g/m$^2$) | 5 | 5 | 20 | — | 5 | 5 |
| Basis Weight of Nanofiber Sheet (g/m$^2$) |  | 10 | 10 | 25 | 20 | 25 | 25 |
| Adhesion to Skin |  | good | good | good | good | poor | poor |

*[1]Single-layered nanofiber sheet made of a uniform mixture of water insoluble nanofiber and water soluble nanofiber As is apparent from the results in Table 1, the laminate sheets of Examples (of the invention) exhibit better adhesion to skin than those of Comparative Examples.

The invention claimed is:

1. A nanofiber laminate sheet comprising:
a layer of a water insoluble polymer nanofiber; and
a layer of a water soluble polymer nanofiber contacting the layer of the water insoluble polymer nanofiber,
wherein the layer of the water insoluble polymer nanofiber does not contain a water soluble polymer nanofiber,
wherein the layer of the water soluble polymer nanofiber does not contain a water insoluble polymer nanofiber,
wherein the layer of the water soluble polymer nanofiber contains a cosmetic component or a medicinal component,
wherein the layer of the water insoluble polymer nanofiber contains a composite nanofiber comprising a nanofiber and a particle fixed to the nanofiber,
wherein the particle is selected from a coloring pigment, a platy particle and a light scattering particle.

2. The nanofiber laminate sheet according to claim 1, wherein the layer of a water insoluble nanofiber comprises a nanofiber of a water insoluble polymer containing a coloring pigment, and
the nanofiber laminate sheet is for use as a cosmetic sheet for makeup.

3. The nanofiber laminate sheet according to claim 2, having an outer color with a hue of 5.0R to 9.8YR, a value of 5.0 to 8.0, and a chroma of 2.5 to 6.0 in the Munsell color system.

4. The nanofiber laminate sheet according to claim 1, wherein the layer of a water insoluble nanofiber contains a composite nanofiber comprising a nanofiber and a particle fixed to the nanofiber, and the particle has a particle size greater than the thickness of the nanofiber and is covered with a material constituting the nanofiber.

5. The nanofiber laminate sheet according to claim 4, wherein the nanofiber of the composite nanofiber has a thickness of 10 to 3000 nm, and the particle has a particle size of 1 to 100 μm.

6. The nanofiber laminate sheet according to claim 4, wherein the particle is a platy particle.

7. The nanofiber laminate sheet according to claim 1, wherein a base sheet is provided on one side of the nanofiber laminate sheet, and the base sheet is releasable from the nanofiber laminate sheet.

8. The nanofiber laminate sheet according to claim 1, wherein the water soluble nanofiber has a cavity, and comprises an oily component.

9. A nanofiber laminate sheet comprising;
a layer of a water insoluble polymer nanofiber; and
a film of a water soluble polymer,
wherein the layer of the water insoluble polymer nanofiber does not contain the film of the water soluble polymer,
wherein the film of the water soluble polymer contains a cosmetic component or a medicinal component,
wherein the layer of the water insoluble polymer nanofiber contains a composite nanofiber comprising a nanofiber and a particle fixed to the nanofiber,
wherein the particle is selected from a coloring pigment, a platy particle and a light scattering particle.

* * * * *